(12) United States Patent
Hoftman

(10) Patent No.: US 8,752,700 B1
(45) Date of Patent: *Jun. 17, 2014

(54) SHARPS CONTAINER WITH BLADE REMOVER, NEEDLE UNSHEATHER, LATCH AND SECURITY ALIGNMENT EXTENSIONS

(76) Inventor: Moshe Mike Hoftman, Calabasas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/403,047

(22) Filed: Feb. 23, 2012

Related U.S. Application Data

(63) Continuation-in-part of application No. 10/706,353, filed on Nov. 12, 2003, now Pat. No. 8,596,453.

(60) Provisional application No. 61/454,477, filed on Mar. 18, 2011.

(51) Int. Cl.
*B65D 85/00* (2006.01)
*B23P 19/02* (2006.01)

(52) U.S. Cl.
USPC ............... 206/355; 29/239; 29/278; 206/359

(58) Field of Classification Search
USPC ............... 206/354, 355, 359, 363, 366, 370; 29/239, 278
See application file for complete search history.

(56) References Cited

U.S. PATENT DOCUMENTS

| | | | |
|---|---|---|---|
| 4,318,473 A | | 3/1982 | Sandel |
| 4,395,807 A | * | 8/1983 | Eldridge et al. ............ 29/239 |
| 4,746,016 A | | 5/1988 | Pollak et al. |
| 4,903,390 A | | 2/1990 | Vidal et al. |
| 5,088,173 A | | 2/1992 | Kromer et al. |
| 5,361,902 A | | 11/1994 | Abidin et al. |
| 5,433,321 A | * | 7/1995 | Abidin et al. ............ 206/354 |
| 5,449,068 A | * | 9/1995 | Gharibian ............ 206/355 |
| 5,729,879 A | | 3/1998 | Hoftman |
| 5,875,532 A | | 3/1999 | Musgrave et al. |
| 5,875,533 A | * | 3/1999 | Henry ............ 29/239 |
| 5,938,063 A | * | 8/1999 | Hoftman ............ 206/370 |
| 6,591,984 B2 | | 7/2003 | Odierno et al. |
| 2004/0111853 A1 | * | 6/2004 | Hoftman et al. ............ 29/239 |
| 2007/0039844 A1 | * | 2/2007 | Zyzelewski et al. ......... 206/363 |

* cited by examiner

*Primary Examiner* — Bryon Gehman

(57) ABSTRACT

The present invention includes a scalpel blade removal device with an opening in a wall defining a first blade guide, extending to a narrowing upward ramp bounded by left and right guide walls. A horizontal top ramp extends from the distal end of the upward ramp, bounded by left and right guide towers. A spring loaded notch device is adapted to lock behind a proximal end of a scalpel blade seated on a scalpel, where the scalpel is inserted in the opening and the blade edge is driven up the ramp to the top ramp. When the notch device is locked behind that end of the scalpel blade, the scalpel is pulled back, causing the scalpel blade to slide off the scalpel handle. A sharps container incorporates the removal device, a reinforced latch, a scalpel resting location, and needle cover removers.

8 Claims, 17 Drawing Sheets

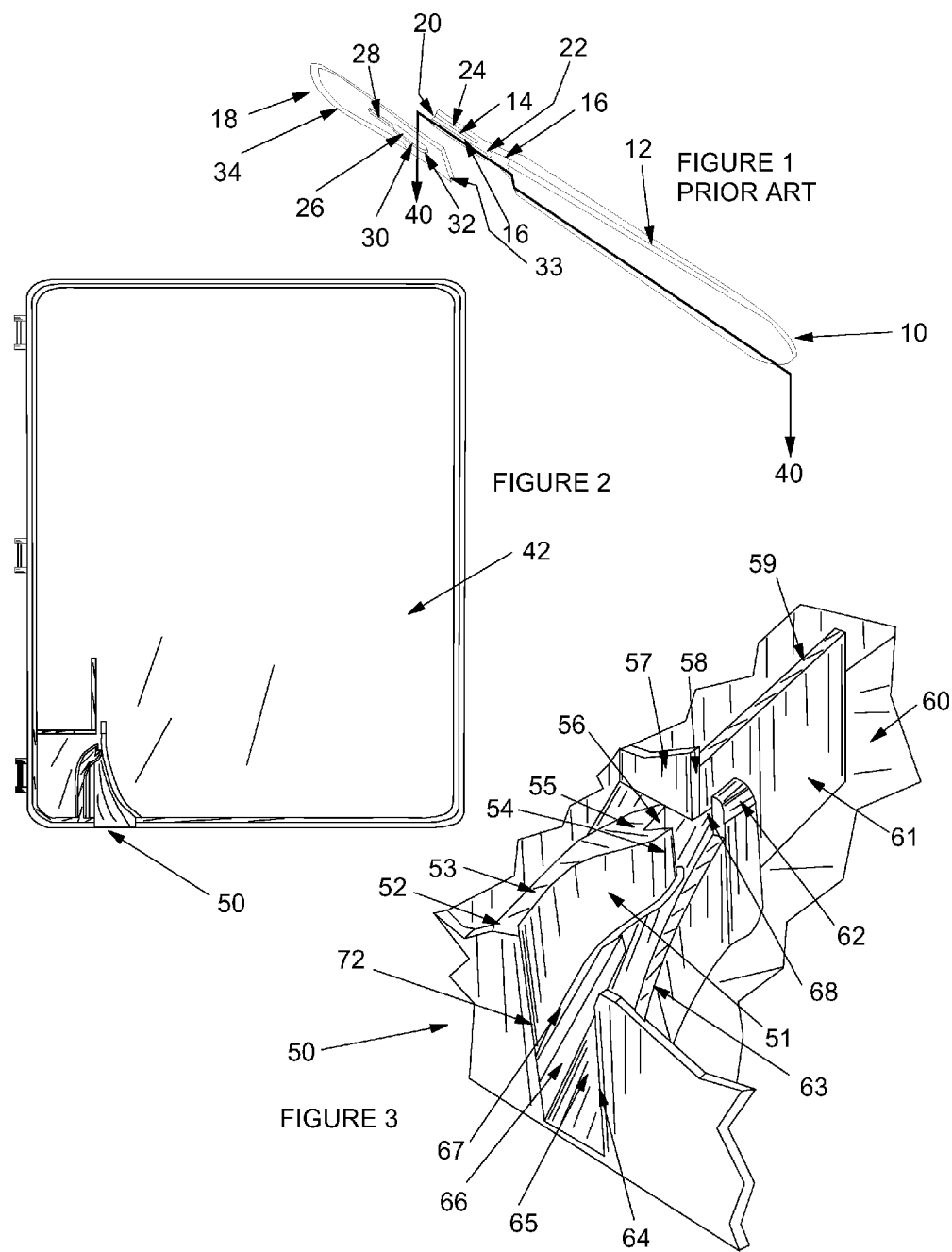

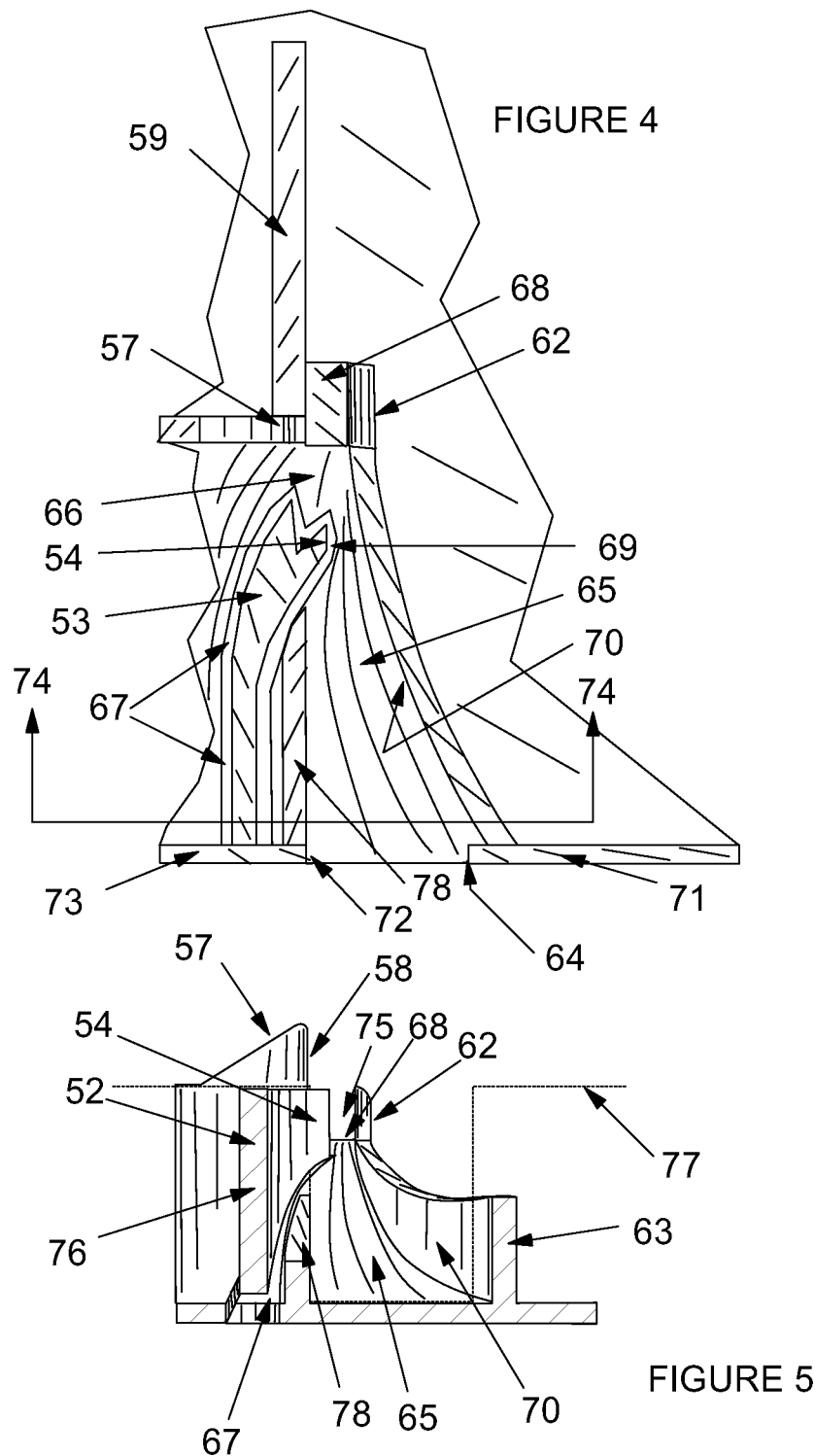

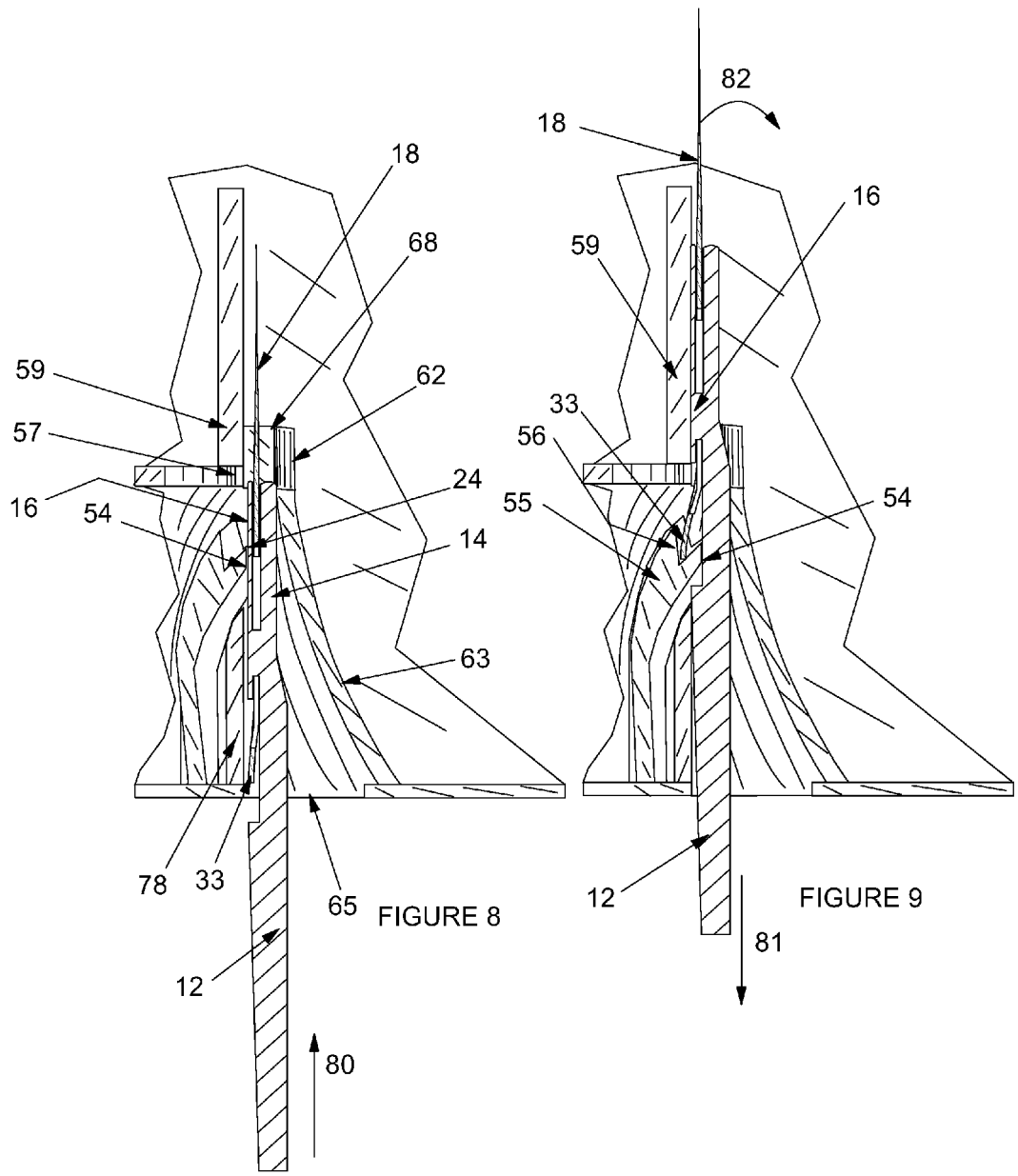

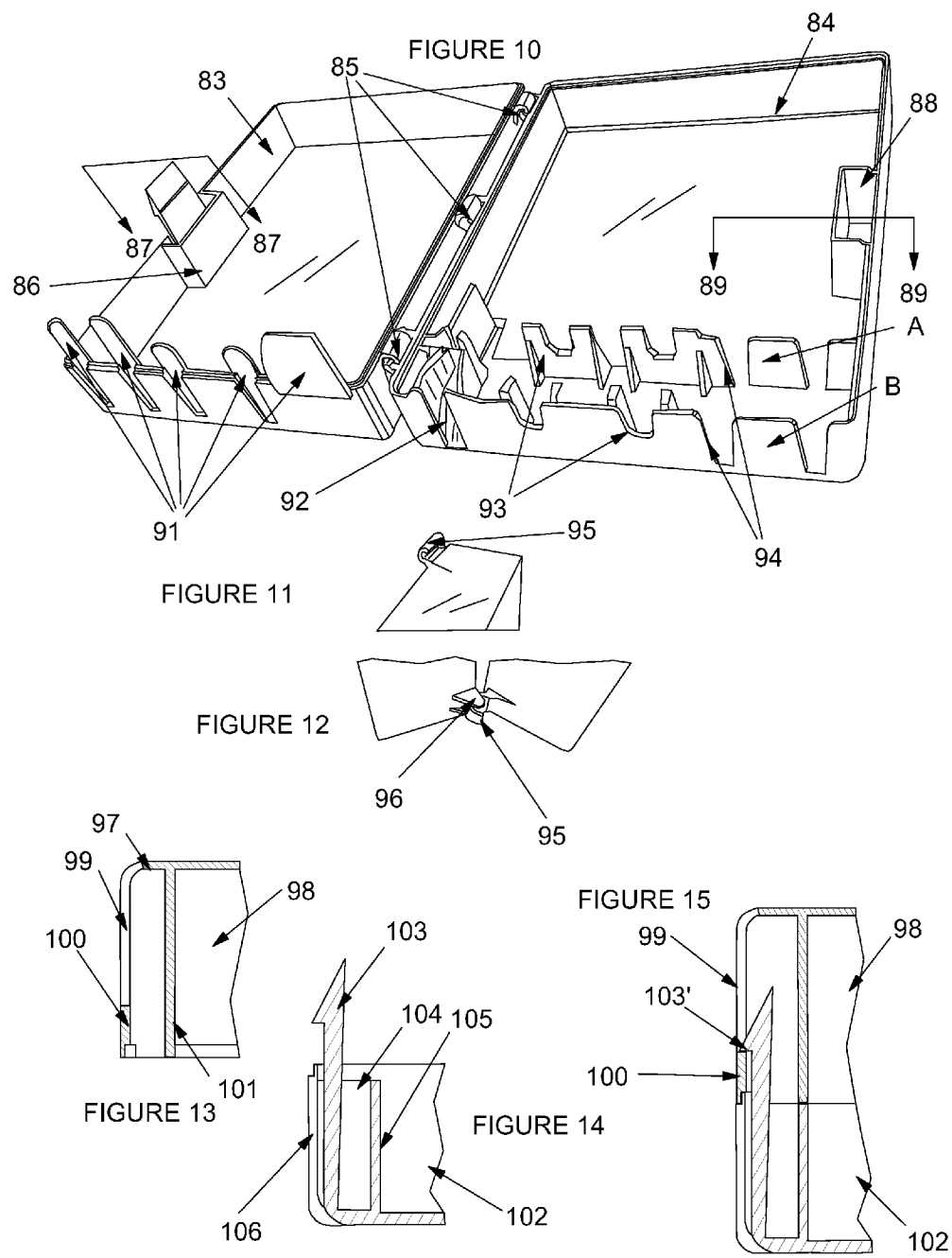

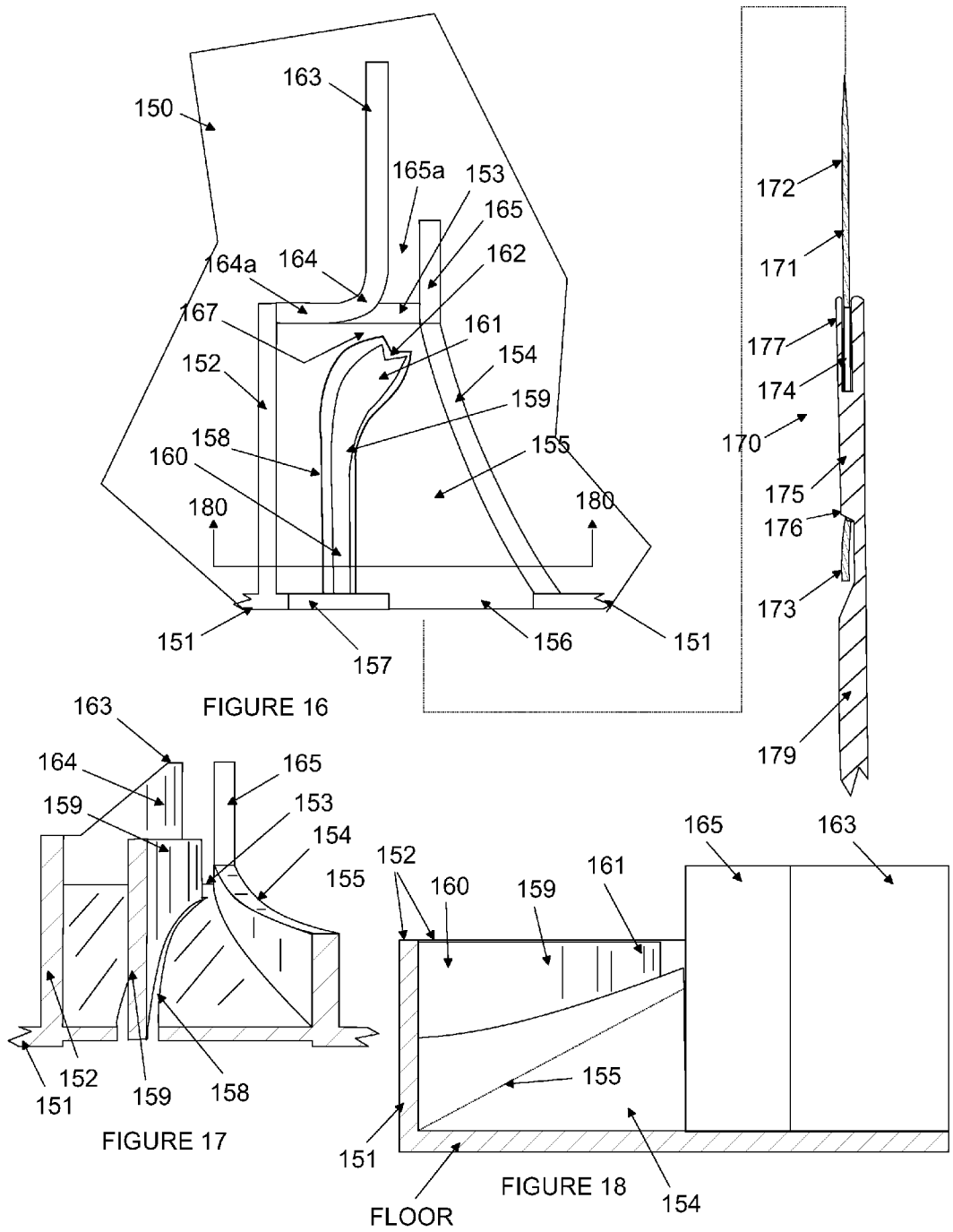

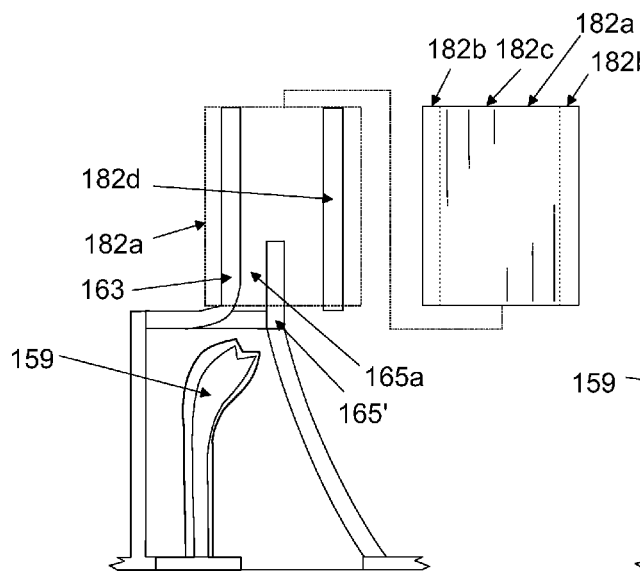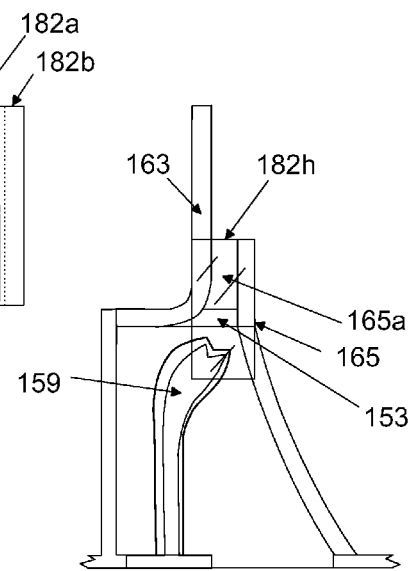
FIGURE 19A
FIGURE 19C
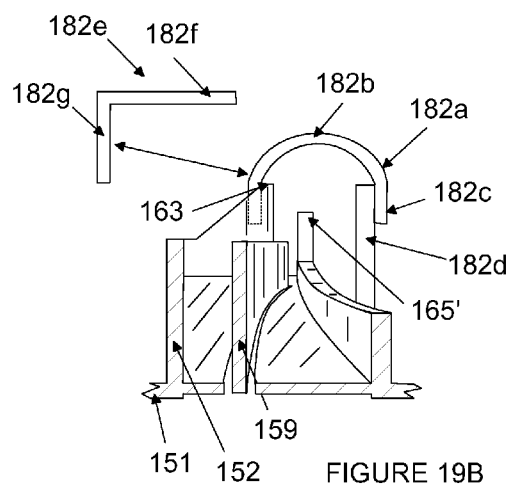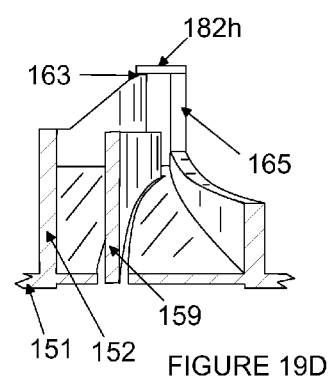
FIGURE 19B
FIGURE 19D

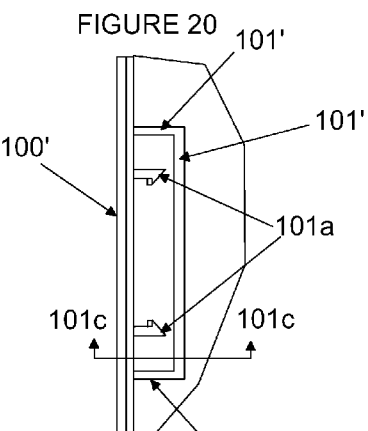
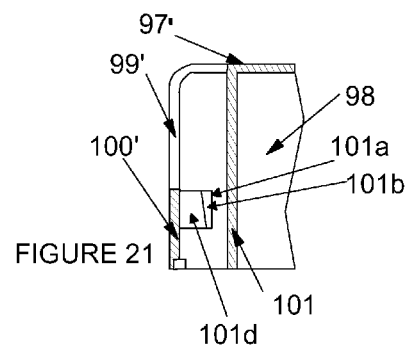
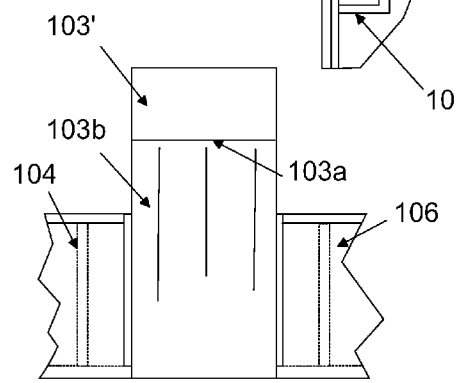
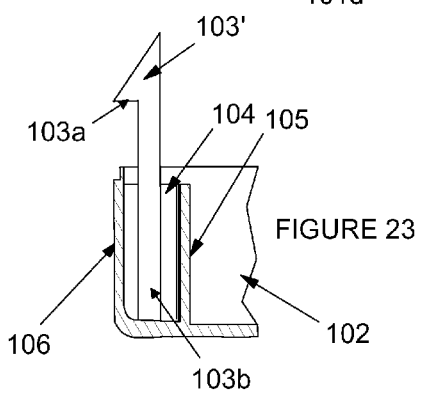
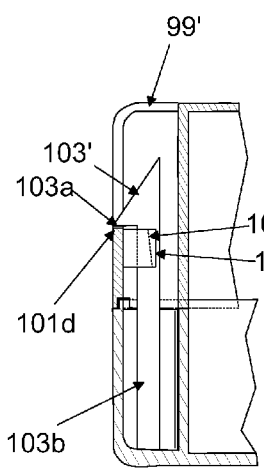
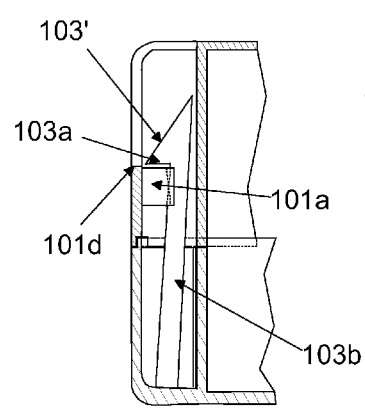
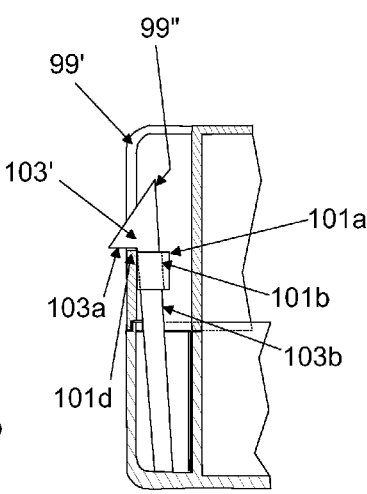

SHARPS CONTAINER WITH BLADE REMOVER, NEEDLE UNSHEATHER, LATCH AND SECURITY ALIGNMENT EXTENSIONS

This application claims the benefit of a provisional application with Ser. No. 61/454,477 filed Mar. 18, 2011, which application is hereby incorporated herein by reference and from which priority is hereby claimed under 35 U.S.C. Sections 119(e) and 120. Further, this application is a continuation in part of the utility patent application Ser. No. 10/706,353, filed Nov. 12, 2003 (Title: Scalpel Blade Remover and Sharps Container; Inventors: Mike Hoftman, William Baer), now issued as U.S. Pat. No. 8,596,453 on Dec. 3, 2013.

BACKGROUND OF THE INVENTION

The present invention relates to the removal of blades from scalpel handles.

During or at the end of a surgical procedure, disposable scalpel blade must be removed from non-disposable scalpel handles. During surgery, some of the disposable blades may get dull or become contaminated and must be replaced by new sharp, sterile blades.

A prior art scalpel handle 10 is shown in FIG. 1 and has a handle portion 12 and a narrow inserted portion 14 connected by a neck portion 16. The inserted portion 14 is located at the forward end of the handle 10 and is adapted to hold a blade 18. The inserted portion 14 has a rounded front end 20 and a rounded rear end 22 with grooves 24 provided around the outer periphery. The blade 18 has a keyed slot 26 with a narrow portion 28 and a wider portion 30 located towards the rear of the slot 26. In operation, the front end 20 of the inserted portion 14 is inserted into the wider portion 30 of the slot 26 and the narrow portion 28 of the slot 26 slides in the grooves 24 until the rear of the slot 26 clears the rear end 22 of the inserted portion 14, at which point the blade 18 is fitted in place on the inserted portion 14. When the blade 18 is in its normal position on the inserted portion 14 of the handle 10, the rear end 22 of the inserted portion 14 engages a rear edge 32 of the blade slot 26, which prevents the blade 18 from moving along its slot 26 along the grooves 24 of the inserted portion 14.

In a simple but dangerous maneuver, to remove a blade 18 from the knife handle 10, a nurse will typically use a surgical tool or his or her fingers to disengage the rear edge 32 of the slot 26 of the blade 18 from the rear end 22 of the inserted portion 14 of the handle 10, and then begin sliding the blade slot 26 along the inserted portion 14. This results in an uncontrolled bending of the blade 18 within its elastic limit so that when the inserted portion 14 reaches the wider portion 30 of the slot 26, the blade 18 has a tendency to snap upward. Such bending and sliding of the blade is dangerous because it may cut the nurse. The blade may also be propelled away from the operating area where someone would have to retrieve. The blade may then be lost temporarily. Furthermore, while removing a blade 18 from a handle 10, the nurse's hand may be cut if his or her hand accidentally slips along the blade 18.

Thus, there is a need to facilitate the safe removal and disposal of blades from surgical knife handles. One such attempt to address this problem is the surgical blade removal and disposal device disclosed in U.S. Pat. No. 4,318,473. This patent discloses the use of a blade removing portion which has a guide integral with a case for guiding the handle and its associated blade therethrough. The guide includes a slot deeper than the handle for receiving the handle and for permitting the handle to move downward. The guide also includes a shoulder positionable under the blade for supporting the rear of the blade. When the handle moves downward in the slot, the inserted portion pulls the central portion of the blade down causing it to bow on the shoulder and the forward portion of the case releasing the rear edge of the blade between the blade slot and the handle and permitting the slot of the handle to slide on the inserted portion. The guide also has a stop integral with the case rearward of the shoulder and above the top of the blade prior to bowing the blade for engaging the rear of the blade. The stop also functions to prevent rearward motion of the blade when it is bowed so that the inserted portion moves in the slot to a wider portion of the slot thereby disengaging the blade from the handle. An abutment forward of the guide and integral with the case positioned over the forward portion of the blade and a guard over the rear of the blade prevent the forward and rear portions of the blade from snapping off the case when the blade is disengaged from the inserted portion.

However, this surgical blade removal and disposal device suffers from a number of drawbacks. First, in order to facilitate safe and proper removal of blades, the blade must be placed at a proper angle in the guide means to allow the blade removal operation to take place. Second, the blade must be aligned appropriately within the guide means. Third, although a larger blade may be removed by this surgical blade removal and disposal device, the removal of such large blades requires bending and twisting of the handle and the blade, which is both dangerous and difficult.

In U.S. Pat. No. 5,729,879 discloses a blade removal device with a blade seat for receiving the blade, a handle seat for receiving the handle, a dividing wall provided between the blade seat and the handle seat and having a sharp curved edge for separating the blade from the handle, and a restraining wall for restraining the blade from rearward movement once the blade has been positioned in the blade seat and the handle withdrawn rearwardly. The present inventor has found that his design in this patent needed improved guidance for the handle and blade. The present inventor also found that the entirely rigid device was in some instances difficult to operate to remove a scalpel handle.

In addition to the safe removal and disposal of surgical blades, the surgical staff must maintain strict accountability for all surgical sharps and/or instruments to ensure that none remain in the patient after surgery, or that none of the surgical sharps and/or instruments are lost or lying around the operating room which may cause injury to the unwary. After removal of a blade, it is placed in a disposal unit so that an accounting can be made of the disposed blades and other sharp objects which when added to the unused blades must equal the number of all blades brought into the surgery.

SUMMARY OF THE INVENTION

The present invention is a scalpel blade removal device. This device gives the user a relatively broad opening into which the user inserts the bladed end of the scalpel. The broad opening extends to a sliding ramp, where, after inserting the bladed end into the broad opening, a forward-driven blade edge moves up the sliding ramp. When the user hits the end of the sliding ramp to come to rest on a top ramp, the user merely pulls rearward on the scalpel handle to pull the blade safely free.

More specifically, the invention comprises a broad opening in a sidewall. The sidewall can be located in any convenient location, although a preferred location is a sidewall of a disposable sharps container, as shown in U.S. Pat. No. 5,729,879.

This broad opening is a first blade guide. This first blade guide has generally vertical edges preventing sideways slipping of the blade or handle when a user inserts the bladed end of the scalpel into it. Immediately adjacent to and extending from the broad opening, a narrowing upward ramp is bounded by left and right guide walls.

A broad opening extending to a narrowing upward ramp bounded by left and right guide walls causes the bladed end of a scalpel to be forced from a broad path to a tightly controlled one as the blade edge slides up the upward ramp. The user avoids having to use extreme care to put the scalpel into a relatively narrow path and keep it there. A horizontal top ramp extends from the distal or top end of the upward ramp. An entry to this top ramp is bounded by left and right guide towers.

In the operation of removing a blade from a scalpel handle, a spring loaded notch device is fixed to the left side of the left guide wall. The notch device is adapted to lock behind a proximal end of a scalpel blade as it passes by the notch device on its way up the upward ramp. The blade at this stage is fixed on the scalpel handle, but can be removed quite easily once the notch device locks onto the scalpel proximal end of a scalpel blade as it passes by the notch device on its way up the upward ramp. Thus, the invention blade remover is simple to operate. Blades are easily removed from scalpel handles in a safe and simple operation.

A sharps container incorporates the removal device, a reinforced latch, a scalpel resting location, and needle cover removers. The sharps container has an upper half and a bottom half connected by three hinges. The upper half and the bottom half are then opened or closed, where the closed position causes a secure latch to keep the container closed. Magnetic sheets line the bottom half for retaining the blades and other sharps. In one form, counting indicia are printed on the magnetic sheets for counting blades and other sharps that are to be disposed. A pad lines the upper half with counting indicia are printed on the pad to count needles and other small sharps.

This disposable sharps container is a unitary, low cost plastic case which sits flat on any surface. Once all the blades have been removed and placed in the sharps container, the sharps container is easily and effectively sealed so that it does not open and expose the blades and/or other sharp objects such as hypodermic needles or suture needles to the environment.

BRIEF DESCRIPTION OF THE DRAWINGS

FIG. 1 is a perspective view of a prior art non-disposable scalpel handle and a disposable blade separated from the handle.

FIG. 2 is a top view of a bottom half of a disposable sharps container box with the invention blade remover incorporated into its side wall and adjacent floor.

FIG. 3 is a perspective and broken away view of the invention blade remover.

FIG. 4 is a top view of the device of FIG. 2 with the notch device in an unflexed position.

FIG. 5 is a cross section 74 view of the device of FIG. 4.

FIG. 8 is the view of FIG. 6 with a scalpel handle and connected blade inserted in the blade remover, with the left side of the scalpel end and blade pressing back the notch device.

FIG. 9 is the device of FIG. 8 with the scalpel handle pulled rearward so that a rearmost edge of the blade is effectively engaged in the notch device.

FIG. 10 is a perspective view of a disposable sharps container with a hinged top and bottom parts of a disposable sharps container with the invention blade remover, hypodermic needle sheath removers, scalpel rests, secure sidewall closures for the openings of the invention blade remover, hypodermic needle sheath removers, and scalpel rests, and secure latch means.

FIG. 11 is a perspective view of a U-shaped part of the hinge of the box of FIG. 10.

FIG. 12 is perspective view of the hinge of the box of FIG. 10.

FIG. 13 is cross section 89 of the latch means of the box of FIG. 10.

FIG. 14 is cross section 87 of the latch means of the box of FIG. 10.

FIG. 15 shows the cross sections of FIGS. 13 and 14 joined in a closed position of the latch means of the box of FIG. 10.

FIG. 16 is a top view of an alternate form of the blade remover shown in top view in FIG. 4 and the cross section the scalpel of FIGS. 8 and 9.

FIGS. 17 and 18 are respectively a section 180 view and left side view of FIG. 16.

FIGS. 19A and 19B are respectively top and front views of an alternate form of the blade remover of FIG. 16 having a curved or L-shaped clear barrier top above a forward part of a disengaging zone of the blade remover.

FIGS. 19C and 19D are respectively top and front views of an alternate form of the blade remover of FIG. 16 having a flat clear barrier top above a disengaging zone of the blade remover.

FIG. 20 is a broken away top view of an alternate form of the latch portion of the bottom portion of the box of FIG. 11.

FIG. 21 is a section 101c of FIG. 20.

FIG. 22 is a front view of the latch portion of FIG. 20.

FIG. 23 is a broken away side view of an alternate form of the latch portion of the top portion of the box of FIG. 11.

FIG. 24 are the latch portions of FIGS. 21 and 23 joined in a closed position with a first latch engaged.

FIG. 25 is the assembly of FIG. 23 with the first latch flange disengaged being pushed back to open the box.

FIG. 26 is the assembly of FIG. 23 with the first latch engaged and a second latch engaged by pulling the first latch flange forward to engage a second permanent latch.

DETAILED DESCRIPTION OF THE INVENTION

Figure 6:
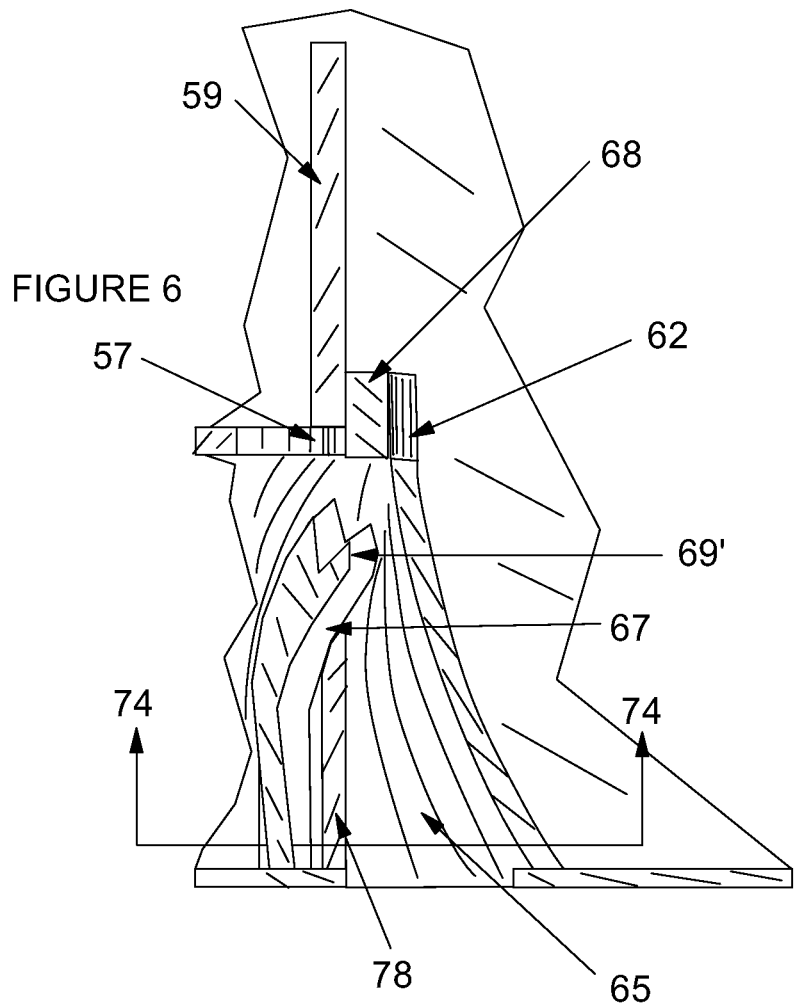
FIG. 6 is a top view of the device of FIG. 2 with the notch device pressed back to receive a back end of a scalpel blade.

The invention is now discussed with reference to the figures.

FIG. 1 shows, as described above, a prior art scalpel handle 12 and blade 18. Section 40 runs along a bottom edge of handle 12 and a mid section of inserted portion 14 and neck portion 16. In FIGS. 8 and 9, section 40 will permit viewing of the operation of the invention blade remover.

FIG. 2 shows a top view of a disposable sharps container 42 with the invention blade remover 50. The blade remover 50 will now be discussed with reference to FIGS. 3 through 7 that show several aspects of blade remover 50.

Blade remover 50 comprises a first blade guide is an opening defined by a bottom of upward ramp 65 and sidewall edges 64 and 72. It is through this opening that the forwardmost part of the bladed end of the scalpel is inserted in a first operating step of the blade remover. A particularly critical aspect of the invention is upward ramp 65. Ramp 65 extends upward from about a 15 to 75 degree angle relative to a floor of a sharps container 42 (FIG. 2). Ramp 65 extends from its lowest and broadest point at the opening forming the first blade guide upward to its highest and narrowest point at its intersection to top ramp 68. In operation, blade edge 34 will slide from the lowest to highest point of ramp 65 and thereafter to rest on top ramp 68.

Upward ramp 65 is bounded on its right side by curved wall 63, where the surface 70 (shown in FIGS. 4 and 5) abuts the right side of blade 18 or scalpel handle 10 as the scalpel is inserted into the invention blade remover. Upward ramp 65 is bounded on its left side in part by a low wall 78, where the surface 66 abuts the blade 18 as the scalpel is inserted into the invention blade remover. Low wall 78 is only part of the guiding means for the blade and scalpel handle as they are inserted into the blade remover. Flexible wall 53 extends inward from an attachment 52 with a sidewall. Attachment 52 is near to edge 72. Flexible wall 53 comprises a surface 51. Flexible wall surface 51 combines with low wall surface 66 to abut a left side of blade 18 or scalpel handle 10 as the scalpel is inserted into the invention blade remover. Flexible wall surface 51 combines with low wall surface 66 to provide as effective guiding means for a left side of the scalpel as surface 70 (shown in FIGS. 4 and 5) provides for the right side of the scalpel.

However, flexible wall 53 serves a more important function than guiding a right side of the scalpel in operation of the blade remover. At the end of flexible wall 53 is notch 56 at short end 55. Notch 56 is the notch that is urged into position behind back end 33 of blade 18 (FIG. 1) that will retain blade 18 in place while scalpel handle 10 is pulled free from blade 18.

Figure 7:
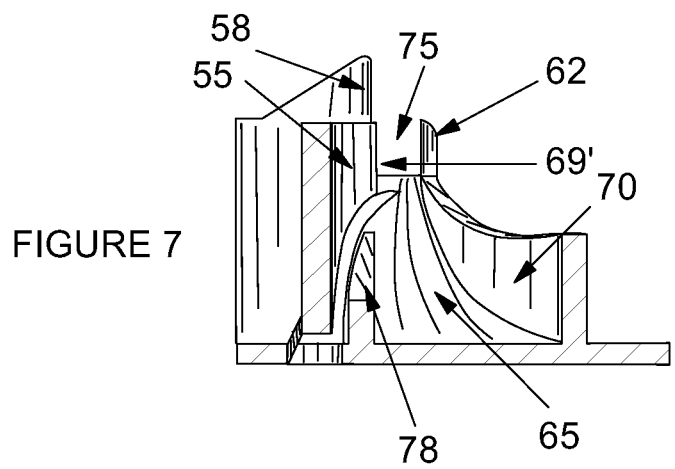
FIG. 7 is a cross section 74 view of the device of FIG. 6.

The structure of flexible wall 53 is unique. At attachment 52, flexible wall 53 has a vertical height of about the height of the sidewall. At short end 55, the vertical height is about from one tenth to about two thirds the vertical height of the sidewall. Cutout 67 extends around the lower periphery of flexible wall 53 except at attachment 52. Thus, flexible wall is free to move in a side to side motion like a tightly spring loaded swinging door. FIGS. 4 and 6 show that distal end 54 can be pressed sideways respectively in directions 69 and 69'. FIG. 4 shows flexible wall 53 in a rest state. FIG. 6 shows flexible wall 53 after it has been pressed left. FIGS. 6 and 7 show the position of flexible wall 53 after a blade and scalpel handle have been inserted into the blade remover. This operation is discussed in more detail with respect to FIGS. 8 and 9.

Flexible wall 53 is cleverly formed during a single molding step with the rest of sharps container box 42 (FIG. 2). The peripheral cutout 67 provides the insertion point for the support wall of the mold for the sides of flexible wall 53.

At the top of upward ramp 65 is top ramp 68. Horizontal top ramp 68 is bounded on the left by edge 58 of lateral extension 57 and a right surface of wall 59. Horizontal top ramp 68 is bounded on the right by a left surface of tower 62. The left and right side boundaries of top ramp 68 continue the guiding means for the blade and scalpel handle as they slide off of the upward ramp 65 and onto top ramp 68.

Operation of the blade remover is now discussed with reference to FIGS. 8 and 9. FIGS. 8 and 9 use a section 40 of scalpel handle 10 with blade 18 (FIG. 1) so that operation of the blade remover is easily seen. FIG. 8 is a view of the operation of the blade remover after:

1. a user holding the handle 10 has inserted the tip of blade 18 into the opening of the first blade guide;
2. the user continues insertion of the scalpel into the blade remover so that edge 34 of blade 18 slides up ramp 65 and almost to top ramp 68;
3. the scalpel has traveled from a broad path at the first blade guide to a narrow path toward the top of upward ramp 65; and
4. in traveling to the narrow path, a left side of the scalpel presses against surface 54 to move flexible wall 53 to the position shown in FIGS. 6 and 7.

FIG. 9 is a view of the operation of the blade remover after:
1. the user continues insertion of the scalpel so the edge 34 of blade 18 rests on top ramp 68;
2. the back end 33 of blade 18 passes by notch 56, whereafter surface 54 springs into contact with neck 16 immediately behind back end 33; and
3. the user pulls back on handle 10 so that back end 33 firmly engages notch 56.

FIG. 9 shows that blade 18 is fixed in the blade remover. The user then continues to pull back on handle 10, causing blade 18 to remain in place as shown in FIG. 9 and eventually disengage from handle 10 entirely. When blade 18 has disengaged from handle 10, blade 18 falls harmlessly along path 82 into the sharps container.

The above blade remover is a dramatic advance in the art. A scalpel is guided from a broad opening to a narrow path that forces the scalpel to push back the notched end of a flexible wall, where the back end of the blade is caught in that notch. Blade removal is a safe and simple operation thereafter.

FIGS. 10 through 15 show a sharps container with a top 83 and bottom 84. Three hinges 85 are formed from U-shaped half 95 on bottom 84 and laterally supported pivot rods 95. Hinges 85 permit top 83 and bottom 84 to be separated. Hinges 85 are operated so that top 83 can close with an almost hermitic seal to bottom 84. Extensions 91 are adapted to closely seal openings for blade remover 92, needle sheath removers 93, and two side by side scalpel rests 94 in bottom 84. The tight sealing of top 83 to bottom 84 prevents any sharps contained in the closed box from being shaken so that a sharp point emerges from the box to harm medical personnel.

Each of the two scalpel rests 94 comprise two aligned notches. One aligned notch is made in box sidewall B and the other aligned notch is in an interior wall A. The notch in sidewall B is aligned with a notch in wall A so that a scalpel with handle and blade can be rested in those notches. A rearward part of the scalpel handle is supported on a bottom edge of the handle in the notch in sidewall B. A more forward part of the scalpel handle and/or its blade are supported at a bottom edge in the notch in wall A. The scalpel rests are extremely important to a surgical procedure. For a long, long time, surgeons and nurses have not had a place to safely and temporarily store a bladed scalpel. If the bladed scalpel is laid down on a surgical tray or on a table top, its straight structure makes is subject to being swept along by movement of gauze or hemostats. In addition, if the scalpel lays flat on a table top or Mayo tray, the blade is raised and exposed, and a practitioner can accidentally move their gloved hand across the raised blade and cut themselves. That sweeping often means the scalpel ends up on the floor or may cut a surgeon's or assistant's hand. The present scalpel rests eliminate that risk by providing a place to temporarily store bladed scalpels with other sharps. This temporary storage forces personnel to pay careful attention to a central location for all stored sharps, including needles and blades.

Latch means for the sharps container comprise top extension 86 and bottom receiver 88. Sections 87 and 88 show the latch means in more detail. Top extension 86 comprises a shield box 105 that extends from the sidewalls 102 of top 83. A similar shield box 101 extends from the sidewalls 98 of bottom 84. These shield boxes prevent sharps contained in the closed sharps container to emerge from or harm a person who will re-open the sharps container. FIG. 13 shows that opening 99 is generally made in the sidewall bounded by shield box 101 so edge part 100 forms a generally straight edge for engaging a lip 103' of extension 103 of receiver 88. An opening 106 is formed in sidewalls 102 for molding of extension 103 as attached to the floor edge of top 83. FIG. 15 shows the sharps container of FIG. 10 in a closed position. In a box closing operation, a tip of extension 103 moves past a box edge of receiver 88 until lip 103' springs into engaging connection as shown in FIG. 15. This structure of latch means has proven to be surprisingly effective in preventing opening of the sharps container after dropping or striking with a heavy object.

Alternate Blade Remover Embodiment

FIG. 16 is a top view of an alternate form of the blade remover 150 shown in top view in FIG. 4 and the cross section of the scalpel FIGS. 8 and 9. A basic box structure comprises ramp support walls 152, 153 and 154, each supporting a ramp 155 (preferably from 30-60 degrees from the floor of the box into which it is integrated) extending down from wall 153 to the outer edge of the box at outer box walls 151 and raised box wall 157. Ramp 155 defines a cutout 158 into which arcuately extends notched extension 159 from a connector wall 160 distally to notched end 161, which defines a notch 162 with which to engage a blunt end of a scalpel blade for removal, as shown in FIGS. 18A through 18H. Referring again to FIG. 1, a free edge of walls 151 and a free edge of wall 157 define an opening 156 whose immediate floor is a front edge of ramp 155. Connector wall 160 extends from a lower position at wall 157 to its top so that notched extension 159 rises to a sufficient elevation to engage a scalpel blade, as described above for a first embodiment of the blade remover.

Critical changes are made in the blade remover 150 as compared with a first embodiment of the blade remover. Left guide wall 163 is extended upward. Right guide wall 165 is extended inward and upward to the same level as right guide wall 163, defining guide space 165a. Left guide wall 163 is curved convexly at section 164 to transition to section 164a. Formation of the guide space 165a provides precise impression of a rear edge of a scalpel blade still connected with a scalpel into the notch 162 during operation of the invention blade remover, in that the opposing surfaces of walls 163 and 165 prevent side to side movement of the scalpel handle and blade assembly. A lower left wall from the first embodiment of the blade remover is removed as well.

Further, a distal notched end 162 of notched extension 159 is extended to within a short distance from an inside surface of wall 153. The filleted corner of wall 163 allows for flexing of the engaged rear edge of the scalpel blade for removal. Moving the notched end 162 of notched extension 159 to within a short distance from an inside surface of wall 153 results in a more instantaneous fall of a front edge of the removed blade onto the box floor and thereafter to a magnetic sheet thereon. It is further critical that the invention blade remover be incorporated into a surgical and medical sharps container box, specifically incorporated into an external wall of a bottom half of such sharps container box so that a removed scalpel blade is adequately secured to a bottom floor of said sharps container box by way of a relatively thin magnetic sheet affixed to that bottom floor. The instantly described blade removers provide for a relatively longer left guide wall 163 opposed to a shorter right guide wall 165 with an elevated (about 0.25 to 1.5 inches above the bottom floor) wall 153 top edge at guide space 165a, understanding that said structure results first in a disengaged blade falling tip first onto said bottom floor, whereafter automatically or with slight forward motion the removed blade falls to the right, flat upon a receiving magnetic sheet to be secured thereon. Notched extension 159 and wall 154 have between them a portion of ramp 155, the three cooperating after opening 156 to guide a blade-first insertion of scalpel 170 up ramp 155 toward guide space 165a. It is essential for operation of the invention blade remover in a sharps container box that walls 152, 153, 154, 157, 159, 163, and 165 be formed vertically as with sidewalls 151 of the box. As described in the first embodiment of the invention, wall 152 may be incorporated into a sidewall of a sharps container box near a corner thereof.

The entire structure of the invention blade remover is adapted to be formed by continuous molding into the bottom floor and sidewalls 151 of a sharps container box, which is accomplished by way of the just described vertical walls but also by providing cutout 158 for flexing of notched extension 159.

Referring now to FIG. 10 and FIG. 16 and incorporating by reference U.S. Pat. No. 6,591,984 (Title: Needle sheathing and unsheathing safety device), a sharps box is shown incorporating needle sheath removers 93 as shown in the '984 patent. As with the invention blade removers, the needle sheath removers 93 are incorporated into and at openings in lateral sidewalls of a bottom half of a sharps container box. In a further embodiment of the sharps container box with the invention blade remover, it has been found that a mold for the bottom half of the sharps container box may be formed so that openings such as those shown for aspects 92 and 94 are formed at regular intervals along the sidewall B in FIG. 10, whereafter removable mold insert tools are prepared and adapted to be fixed in a desired product configuration. A desired product configuration will allow for forming the invention blade remover at the far left, far right, or intervening openings along wall B of FIG. 10. Thereafter, one, two or more needle sheath removers 93 may be incorporated at remaining openings along wall B. A customer need not accept a single configuration of the bottom half of the sharps container box and may easily be supplied at low production cost (using a single mold adapted for removable insert tools as just described) for a bottom half of a sharps container box having greater or less spacing between the removable insert tools consisting of a blade remover, a needle sheath remover, or a scalpel rest. In a specific example, a user may desire only a single needle sheath remover (at a far right position along wall B) with an invention blade remover (at a far left position along wall B, as in FIG. 10) to provide maximum distance between users' hands engaged in operating those features. In another specific example, a user may desire, being right handed, to locate the invention blade remover at a far right position along wall B so that the user can use their left hand to grasp the bottom half of the sharps container box when disengaging a scalpel blade. There is a need for such an adaptable features sharps container box.

FIG. 1 also shows scalpel 170 having blade 171 with front end 172, rear edge 173, and slot 174 for engaging a handle 179 with a broken away user end portion at blade lock 175, which has top end 177 and rear end 176.

FIGS. 17 and 18 are respectively a section 180 view and a left side view of FIG. 16, wherein ramp 155 can be seen rising rearward, upon which the blade edge of a scalpel will initially impress when urged through opening 156, resulting in said blade being directed to guide space 165a by way of guidance from a concave and distal end of notched extension 159 on the left and curved wall 154 on the right. It will be appreciated that notched extension is flexible toward the left to urged against a left side of a scalpel handle by way of cutout 158 in ramp 155.

Figure 18A:
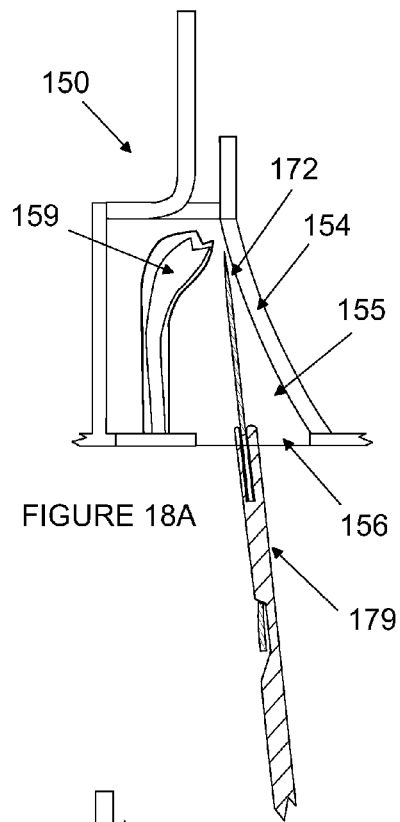
FIGS. 18A through 18H are steps showing the scalpel blade of the scalpel of FIG. 16 being removed with the blade remover of FIG. 16 in steps similar to those of FIGS. 8 and 9.
Figure 18B:
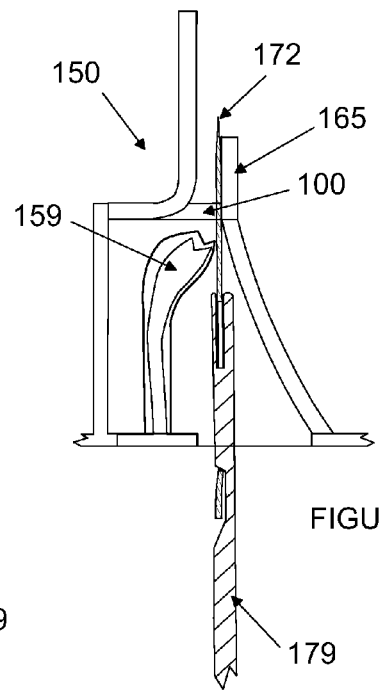
Figure 18C:
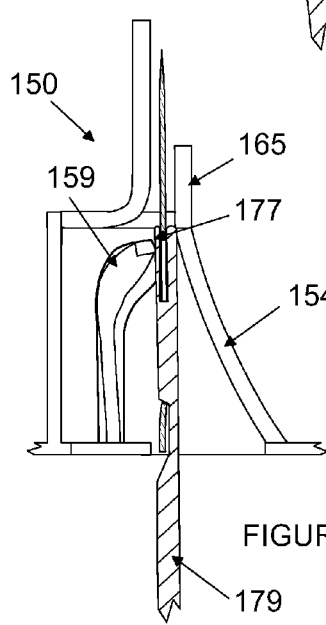
Figure 18D:
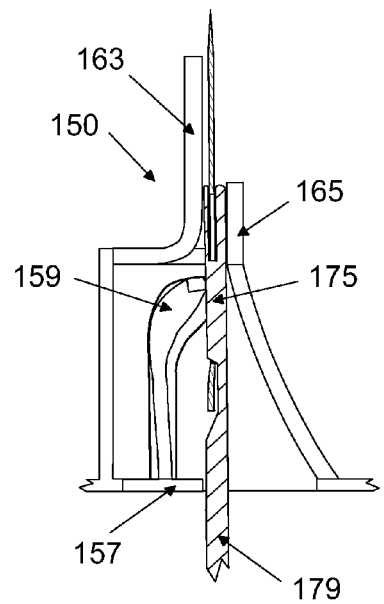
Figure 18E:
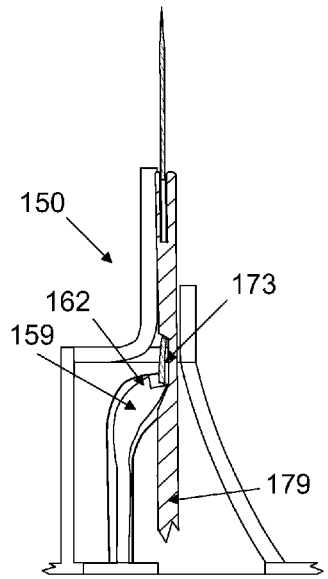
Figure 18F:
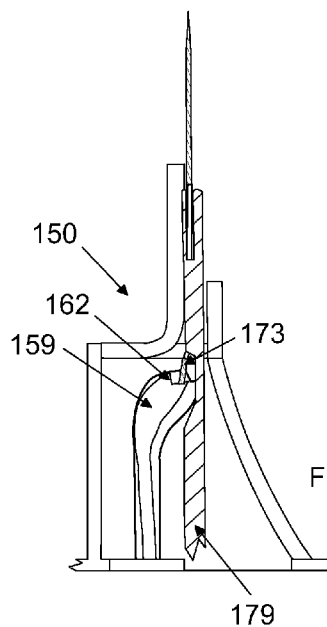
Figure 18G:
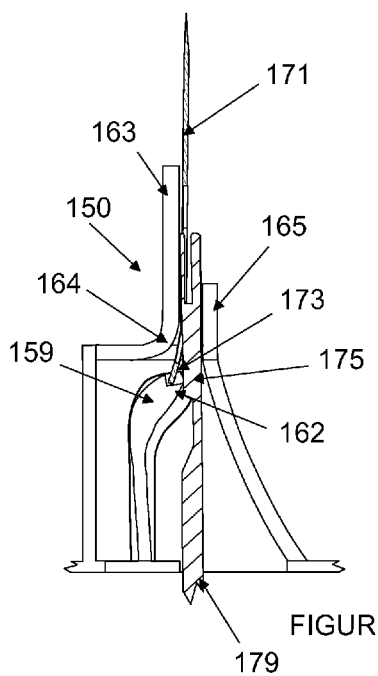
Figure 18H:
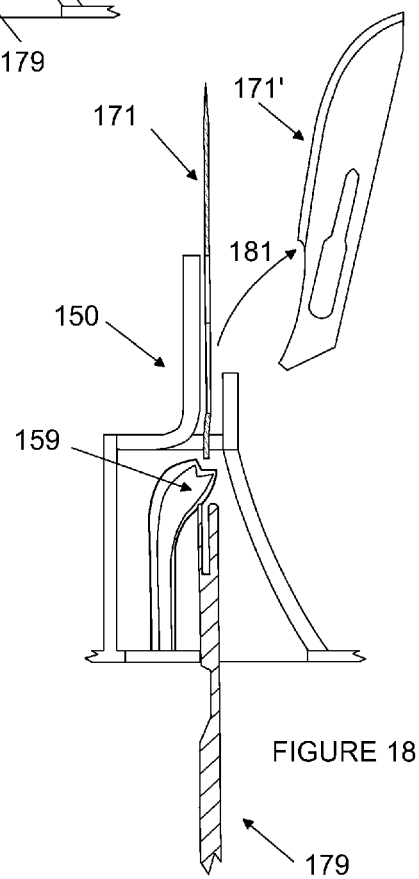

FIGS. 18A through 18H are steps showing the scalpel blade of the scalpel 170 of FIG. 16 being removed with the blade remover 150 of FIG. 16 in steps similar to those of FIGS. 8 and 9. FIG. 18A shows end 172 of scalpel 170 through opening 156 and sliding up ramp 155. FIG. 18B shows end 172 entering guide space 165a, partly directed there by impingement on a distal end of notched extension 159 and wall 165. FIG. 18C shows that end 177 has almost maximally deflected the distal end of notched extension 159 by way of concurrent sliding against wall 154 to wall 165, where in FIG. 18D the distal end of notched extension 159 is maximally deflected with a front end of blade lock 175 tightly and vertically engaged between walls 163 and 165 (as opposed to the substantially reduced vertical fixation of wall 62 of FIG. 4). While extension of wall 165 to at least 25-75% of wall 163 horizontal length is preferred, fixation of the entire orientation of scalpel 170 is further accomplished by abutment of 179 against a right edge of wall 157. FIG. 18E shows further insertion of scalpel 170 into the invention blade remover 150 so that notch 152 engages rear edge 173 as the distal end of notched extension 159 is urged against handle 179, where in FIG. 18F handle 179 is pulled rearward, lifting edge 173 further into notch 162 and in FIG. 18G is shown lifted above the rear end of blade lock 175, whereby filleted section 164 allows for leftward deflection of rear edge 173 to disengage blade 171 from handle 179. Thus, a distal end of notched extension 159 may be located less substantially adjacent or within ¼ inch of wall 153 so that, as shown in FIG. 18H, blade 17 has preferably less than 10% (and more preferably less than 5%) of its length extending rearward over wall 153 after complete disengagement from handle 179, thereby with gravity urging it to fall onto a bottom floor of a bottom half of a sharps container box along path 181 to position 171'

FIGS. 19A and 19B are respectively top and front views of an alternate form of the blade remover of FIG. 16 having a curved clear barrier top 182a or an L-shaped clear barrier top 182 above a forward part of a disengaging zone of the blade remover. Top 182a comprises an upwardly convex section 182c extending down to attaching walls 182b, which walls 182b are attached by adhesive, latch or other connection means at inside surfaces to outside surfaces of walls 163 and 182d. Wall 182d extends vertically upward from a floor of the invention sharps box. A substantial viewing space is defined beneath top 182a when installed, which space provides a user clear viewing of a disengaged blade while top 182a prevents the blade from being ejected upward toward the user or out of the sharps box. Top 182e comprises a horizontally flat section 182f extending down on a left side to attaching wall 182g, which wall 182g is attached by adhesive, latch or other connection means at an inside surface to an outside surfaces of wall 163. A substantial viewing space is defined beneath top 182e when installed, which space provides a user clear viewing of a disengaged blade while top 182e prevents the blade from being ejected upward toward the user or out of the sharps box.

FIGS. 19C and 19D are respectively top and front views of an alternate form of the blade remover of FIG. 16 having a flat clear barrier top 182h above a disengaging zone of the blade remover. Top 182h is fixed by latch, adhesive or other secure fixation to top edges of walls 163 and 165 to provide clear viewing of guide space 165a and the space around a distal end of notched extension 159 for user safety against spring-action release of scalpel blades using the invention blade remover and while inserting the scalpel assembly into the invention blade remover. Clear barrier top 182h prevents upward disengagement from the blade remover of a scalpel handle and blade while applying sometimes substantial forward and rearward force to engage the rear blade edge to the notched extension 159 and thereafter pull the scalpel handle free of the blade.

FIG. 20 is a broken away top view of an alternate form of the latch portion of the sharps container box of FIG. 11 (for which FIG. 22 is a front view), a first re-openable latch and a second permanent lock latch are provided. The first latch is intended to be used where the box may still be in use for receiving surgical and medical sharps but and may be re-opened at a later time in a procedure. There is a need for providing a second, subsequent latch whereby the box is permanently locked shut so that only substantial destruction of the box will release the second latch. Front wall 100' corresponds substantially to the front wall 100 of FIG. 13, but is adapted to include inward directed second latch flanges 101a, the space around which is enclosed and defined by walls 101'.

Referring to FIG. 21 as section 101c of FIG. 20, a side view of second latch flanges 101a are shown having a lower section 101d and a lip section 101b, similar in function to the first latch flange 103' with lower section 103b and lip section 103a in FIG. 23. In FIG. 21, sidewall 100' is increased in vertical height to edge 101d somewhat to accommodate second latch flanges 101a thereon an inside surface. Opening 99' is expanded to accommodate a user's fingertips as described below, moving rearward bottom floor 97'. The invention latch system is shown with the box upside down but may also represent its incorporation in the manner shown in top and bottom halves of a sharps container box.

FIG. 23 is a broken away side view of an alternate form of the latch portion of the top portion of the box of FIG. 11, where a first latch flange 103' with lip section 103a adapted to be urged over edge 101d of FIG. 21 when the box is in the closed position by way of rearward deflection and forward release along lower section 103b, where walls 104 and 105 enclose a space around first latch flange 103', where the first latch is shown in the latched position in FIG. 23. The improvement of a second latch is available by way of second latch flanges 101' each having opposed lip sections 101b impressed upon opposite side edges of lower section 103b in FIG. 24, preventing them from becoming latched to lower section 103b. Further, FIG. 25 shows that a user may press lip section 103a rearward to disengage the first latch and open the sharps container box. Latching and unlatching the first latch may occur as many times as a user desires.

FIG. 26 shows the permanent, locked structure and orientation of elements in the second latch, where a user directs lip section 103a in a forward direction 99" so that lip sections 101b latch by overlapping a backside of lower section 103b of the first latch flange 103'. This shows both the first latch and second latch engaged to prevent opening of the sharps container box. A user cannot disengage the second latch formed by the latching of second latch flanges 101' to first latch flange 103' without substantial force and destruction of the sharps container box.

Figure 27:
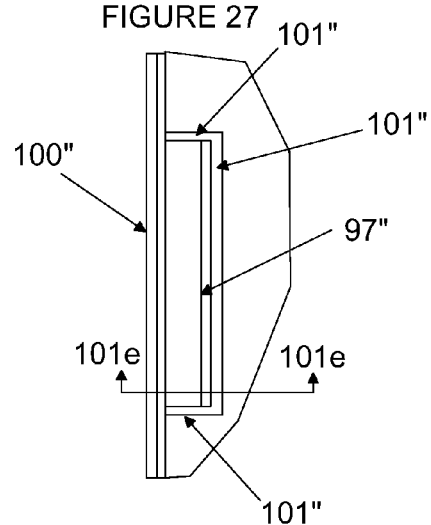
FIG. 27 is a broken away top view of another alternate form of the latch portion of the bottom portion of the box of FIG. 11.
Figure 28:
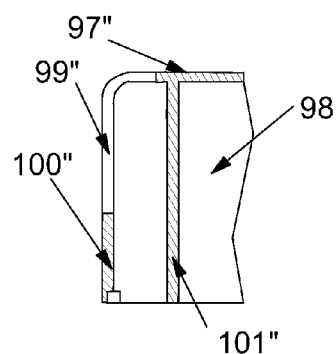
FIG. 28 is a section 101e of FIG. 27.
Figure 29:
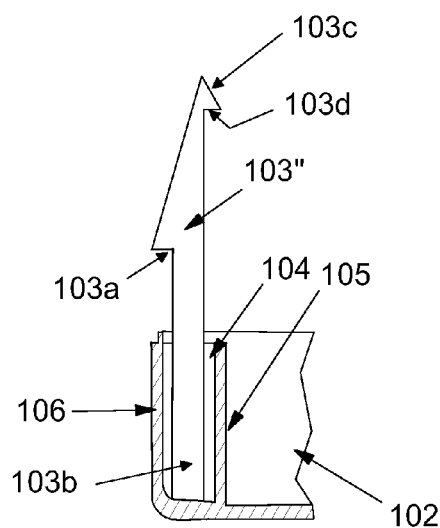
FIG. 29 is a broken away side view of another alternate form of the latch portion of the top portion of the box of FIG. 11.
Figure 30:
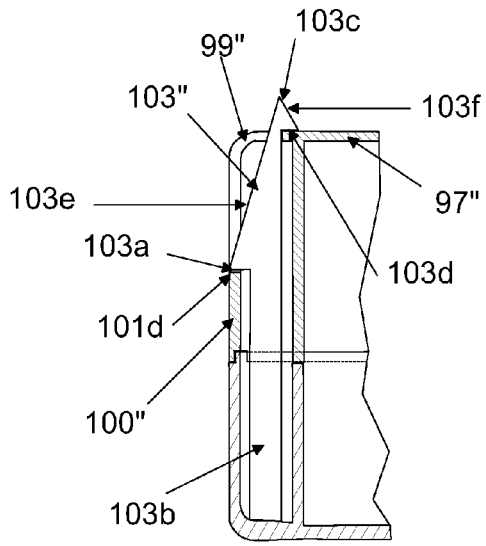
FIG. 30 are the latch portions of FIGS. 28 and 29 joined in a closed position with a first latch and a second latch engaged.

FIG. 27 is a broken away top view of another alternate form of the latch portion of the bottom portion of the box of FIG. 11. FIG. 28 is a section 101e of FIG. 27. FIGS. 20 and 21 are similar to FIGS. 27 and 28, except that box floor 97" is slightly extended over opening 99" in the latter Figures. Front wall 100" lacks inward directed flanges. The broken away side view in FIG. 29 of another alternate form of the latch portion of the top portion of the box of FIG. 11 is similar to that shown in FIG. 23, except that the first latch flange 103" is extended upward to form a second latch extension 103c with second latch lip 103d. FIG. 30 shows that flange 103" passes through a space behind front wall 100" as it moves to a closed position, whereby as lip 103a engages the top of wall 100" the lip 103d simultaneous engages a top edge of box floor 97", resulting in a permanent, dual closure of top and bottom box portions. Moving extension 103c in direction 103f simply further impresses lip 103a over the top of wall 100".

Figure 31:
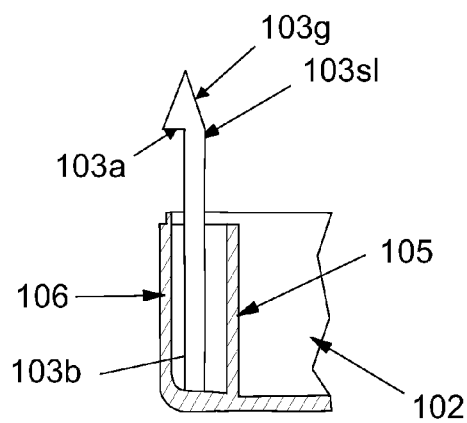
FIG. 31 is a broken away side view of another alternate form of the latch portion of the top portion of the box of FIG. 11.

FIG. 31 is a broken away side view of another alternate form of the latch portion of the top portion of the box of FIG. 11 and is similar to that shown in FIG. 23, except that the first latch flange 103sl is sloped flat down and outward to form lip 103a and is also sloped down and rearward upward to form sloped section 103g.

Figure 32:
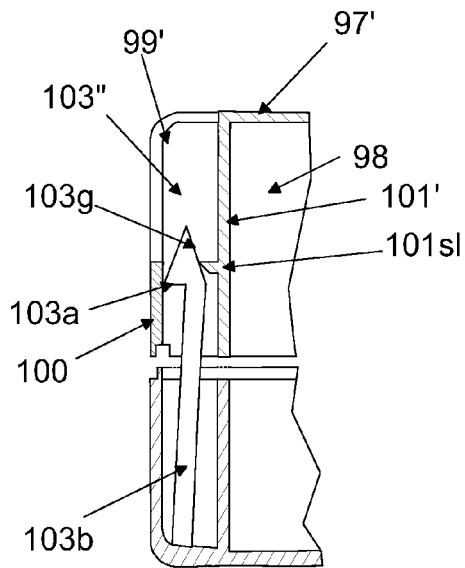
FIG. 32 shows a modified latch portion of FIG. 21 and the latch portion of FIG. 31 at a first step in moving to a closed position.
Figure 33:
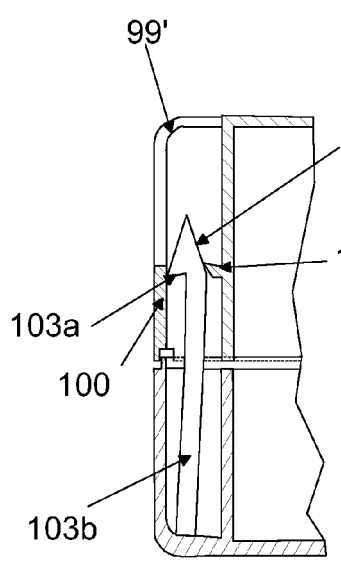
FIG. 33 shows a modified latch portion of FIG. 21 and the latch portion of FIG. 31 at a second step in moving to a closed position.
Figure 34:
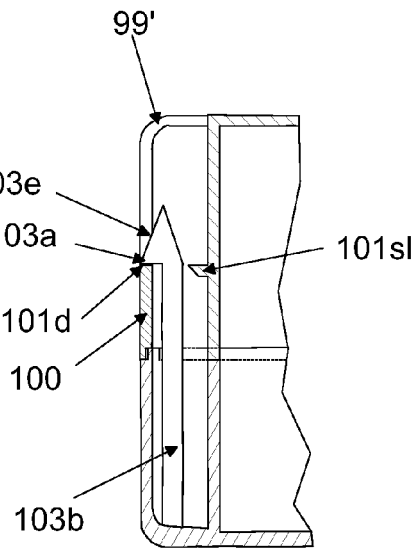
FIG. 34 shows a modified latch portion of FIG. 21 and the latch portion of FIG. 31 at a closed position.

FIG. 32 shows a modified latch portion of FIG. 21 where a horizontal forward extension 101sl is made from an outward surface of a back part of wall 101', where in a first step of moving to a closed position, lip 103a engages an inside surface of wall 100 and sloped section 103g engages extension 101sl. Upon further pressing of the two box portions together in a second step of moving to a closed position, FIG. 33 shows slight deflection of lip 103a and extension 101sl substantially resisting passage of flange 103sl through a passage defined by an inside edge of wall 100 and extension 101sl. FIG. 34 shows a closed and permanently latched position of the two box portions, with lip 103a engaged above a top edge of wall 100. The box in the closed position shown in FIG. 34 is substantially permanently locked.

Figures 35, 36:
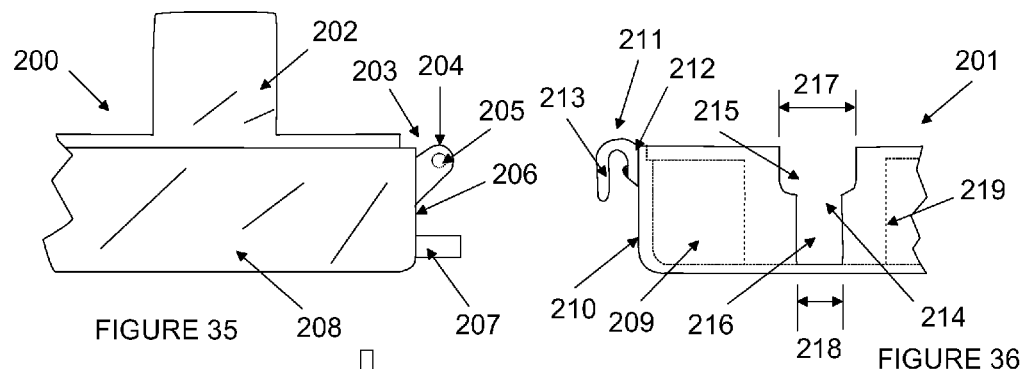
FIG. 35 is a broken away edge view of a back hinge wall of a top portion of the box of FIG. 11 modified with orientation supports protecting outward from the back hinge wall.
FIG. 36 is a broken away edge view of a back hinge wall of a bottom portion of the box of FIG. 11 modified with an extended C-shaped part of the hinge and a side view of a side wall defining an opening adapted for forming behind it an invention blade remover or needle unsheather.
Figure 37:
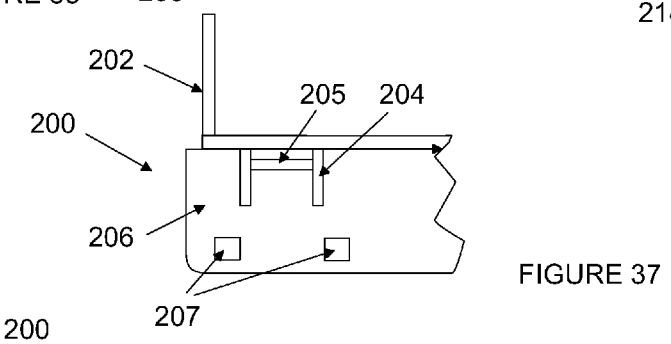
FIG. 37 is a side view of the back hinge wall of FIG. 35.
Figure 38:
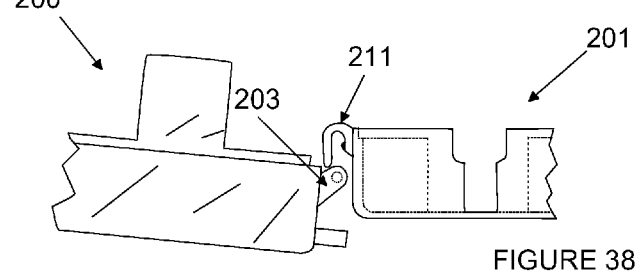
FIG. 38 shows the box portions of FIGS. 35 and 36 at first step of engaging the two parts of the hinges on those box portions.
Figure 39:
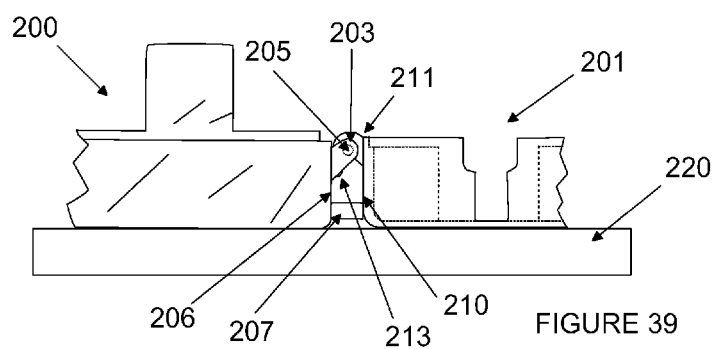
FIG. 39 shows box portions of FIGS. 35 and 36 with the two parts of the hinges on those box portions fully engaged and orientation supports causing the box portions to remain aligned.

FIG. 35 shows a broken away edge view of a back hinge wall 206 of a top portion 200 of the box of FIG. 11 modified with orientation supports 207 protecting outward from the back hinge wall 206. A sidewall 208 supports cover flange 202, which in a closed position covers opening 214 shown in FIG. 36. FIG. 35 shows a first hinge part 203 comprising outward extensions 204 supporting rod 205, which is adapted to be detachably engaged with a C-shaped cross section hinge part. FIG. 36 shows a broken away edge view of a back hinge wall 210 of a bottom portion 201 of the box of FIG. 11 modified with an extension 213 of the C-shaped hinge part 211 extending from the connection section 212. Extension 213 provides additional critical resistance to disengagement of box portions 200 and 201 during use of a blade remover according to the invention, where a user who is right handed would naturally use their left hand to grasp an opened top portion 200 to stabilize the entire engage structure during disengagement of a scalpel blade. Grasping top portion 200 while operating upon bottom portion 201 for disengagement of a scalpel blade could result in disengagement through the opening of the C-shaped hinge part 211 of FIG. 36 of the rod 205 shown in FIG. 37. Such disengagement could disrupt a user's ability to press forward or pull outward a scalpel handle as required for operation of the invention blade remover. The vertically downward extension 213 of hinge part 211 virtually eliminates disengagement when operating the invention blade remover. FIGS. 38 and 39 show engagement (and in reverse, disengagement) steps for hinge parts 203 and 211.

Further, it has been found that maintaining approximate 180 degree alignment of opened box portions 200 and 201 as shown in FIG. 39 is important to a user when lifting the opened box. Supports 207 extending from wall 206 abut wall 210 in the fully opened position, causing the box portions 200 and 201 to remain in approximately 180 degree alignment with respect to each other. A use picking up the opened box portions 200 and 201 shown in FIG. 39 can rely on them remaining in the same position instead of having one side or another fall downward, resulting in spillage of sharps and/or causing an unexpected change weight distribution. The supports 207 would extend from wall 206 from beneath or near beneath hinges at each end of wall 207.

FIG. 36 shows an opening 214 to which can be incorporated any of the invention blade removers or the above described needle unsheathers (alternately identified herein as "needle uncapper or exchanger"), thereby improving upon the method for forming a base form of a bottom portion of a sharps box and later installing in a mold for the base form of a bottom portion of the sharps box a mold tool for forming either one of the invention scalpel blade removers or a needle unsheather at opening 214 as desired by a customer. Opening 214 is defined in side wall 209 to have an upper wide section 215 with a width 217 (adapted for operation of the needle unsheather) and a lower narrow section 216 (adapted for insertion of a scalpel blade and handle as described above for any of the invention scalpel blade removers).

In a further description of the invention scalpel blade remover, a specific form of the invention blade remover is a sharps container box having a separately unitarily molded top half and bottom half incorporating into one of four sidewalls of the bottom half a scalpel blade remover adapted to remove a scalpel blade from a scalpel handle, each scalpel blade having a rear edge which abuts a rear surface of a neck of the scalpel handle in a locking relationship, the handle further having a blade locking portion provided at a front end thereof and grooves provided along the periphery of the blade locking portion, the scalpel blade also having a slot for receiving the grooves of the blade locking portion of the scalpel handle, the grooves being slidable in the slot and passing through a wider opening at a portion of the slot to permit the blade to be removed from the blade locking portion, the scalpel blade remover comprising:

(a) a vertical rectangular opening defined in a sidewall and a bottom floor's edge of the bottom half, extending upward and inward from the bottom floor's edge a ramp at from 30 degrees to 60 degrees to an elevation from 0.25 to 1.5 inches from the bottom floor, the ramp being supported by a left wall, back wall, and right wall;

(b) a notched extension extending rearward from near an inside surface of the sidewall to the left of the rectangular opening, the notched extension being curved at a distal end into a space inwardly normal to the rectangular opening, whereon said distal end is a defined notch inward directed, the notched extension having an elevation greater than the back wall by greater than 0.25 inches, and a cutout is defined in the ramp around the notched extension allowing deflection of said distal end to the left;

(c) a left guide wall extending inward from the back wall, rising from the bottom floor to an elevation more than 0.25 inches above the top of the back wall, and having a right side aligned with a right edge of the rectangular opening;

(d) a right guide wall extending inward from the back wall, rising from the bottom floor to an elevation more than 0.25 inches above the top of the back wall, and having a left side aligned spaced apart from the right side of the left guide wall by a thickness of the blade locking portion;

(e) the right wall extending from a front edge of the right guide wall convexly along the ramp to a right edge of the rectangular opening; and (f) the blade remover is adapted so that:

(i) a tip of a scalpel blade fixed to a scalpel handle may be moved past the rectangular opening to force a bottom edge of the blade to slide up the ramp and come to rest on a top edge of the back wall resulting in said distal end to be deflected substantially to the left; and (ii) the distal end of the notched extension is urged to the right to engage the rear edge of the scalpel blade, whereupon a user draws the scalpel handle outward from the sidewalls to disengage the scalpel blade from the scalpel handle.

Figure 40:
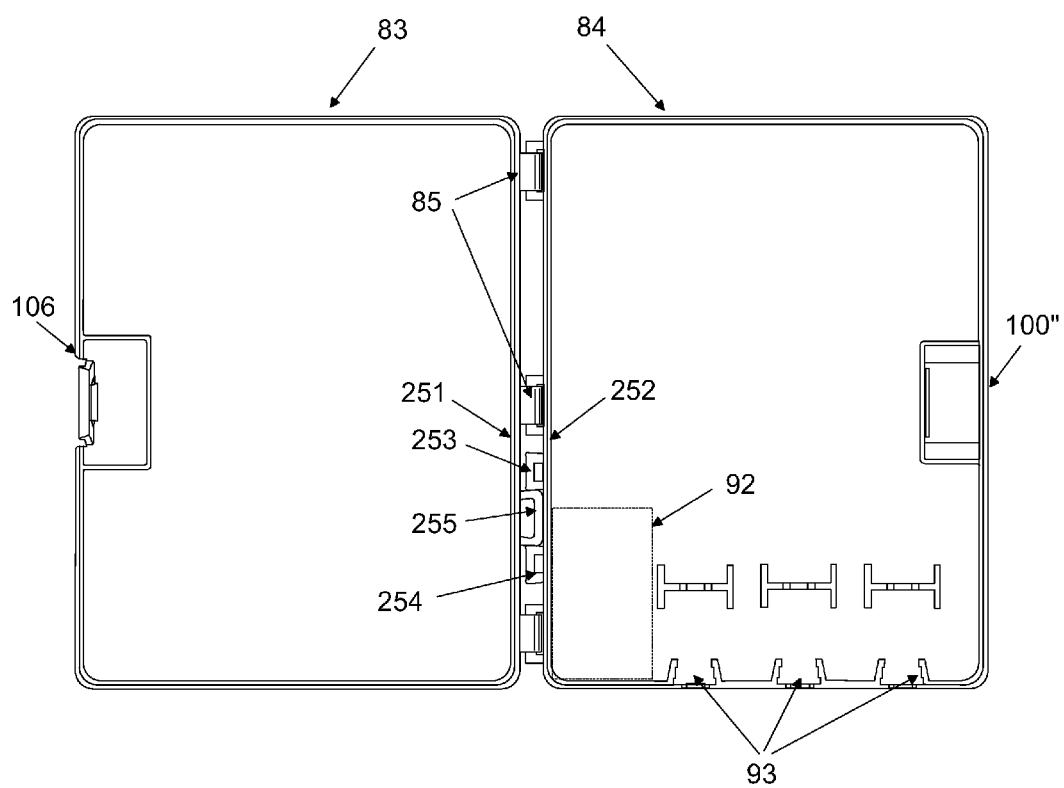
FIG. 40 is a top view of an invention sharps box having engaging extensions from outside surfaces of a rear wall.

In another embodiment of the invention sharps box to provide secure alignment of a fully opened sharps box as shown in FIG. 40, top views are shown of top half 83 and bottom half 84, where are also shown in top view are the secure latching structures shown and described in FIGS. 27 through 30. The arrangement of 3 needle unsheathers 93 with a blade remover at the broken line area 92 is also shown as exemplary of selection of optional mold tools for a base box mold to form such a bottom half 84. Hinges 85 are formed so as to allow disconnection and re-connection of top half 83 from bottom half 84. A further improvement is found in two opposing extensions 253 and 254 extending horizontally from an outside surface of rear wall 252 toward and abutting rear wall 251. These extensions alone will prevent top half 83 from falling downward out of a planar orientation with bottom half 84 when either half is picked up. Further, the two opposing extensions 253 and 254 are spaced apart sufficiently to capture between them the central extension 255, which extends horizontally from an outside surface of rear wall 251 toward and abuts an outside surface of rear wall 252.

Figure 41:
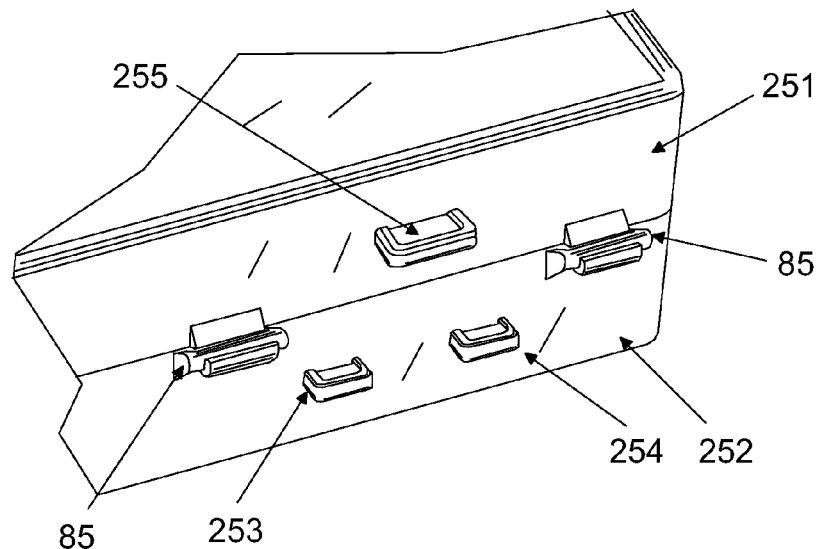
FIG. 41 is a broken away rear perspective view of the closed sharps box of FIG. 40.

Central extension 255 is wider at its free edge which abuts the outside surface of rear wall 251 than at its base, forming two lateral engaging notches which engage similarly formed engaging notches in the two opposing extensions 253 and 254. FIG. 41 is a broken away rear perspective view of the closed sharps box of FIG. 40, where extensions 253, 254 and 255 are shown extending from their respective rear walls without impeding the use of the sharps box for other purposes and without interfering with easy disposal when use is finished.

Figure 42:
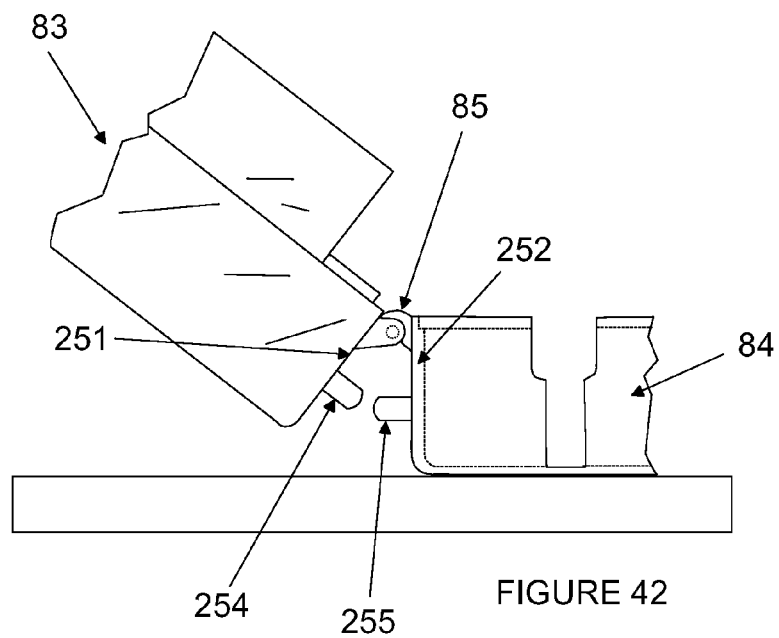
FIG. 42 is a broken away side view of the sharps box of FIG. 40 partly moved apart from a completely opened position.

The advantages of the capture of extension 255 by extensions 253 and 254 include not only certainty of alignment of a top half and bottom half in a fully opened position, but also include security for a user of a scalpel blade remover. A scalpel blade remover adapted to require back and forth motion of a scalpel handle through an opening in a left sidewall of a bottom half of a sharps box typically requires the user to grasp the top half of the sharps box with the left hand to stabilize the bottom half of the sharps box. Without the capture of extension 255 by extensions 253 and 254, the bottom half of the sharps box is more likely to move back and forth or otherwise be unstable for the critical activity of removing the scalpel blade. There is a need for stabilizing means for a fully open top and bottom halves of sharps boxes, as provided by the present embodiment of FIGS. 40 through 42.

In a further improvement in a scalpel blade remover incorporated into and about an opening in a left or right sidewall of a bottom half of a sharps box, FIGS. 43 through 50 show an alternate form of a transparent cover for protection of a user and effective viewing of the blade disengagement steps.

Figure 43:
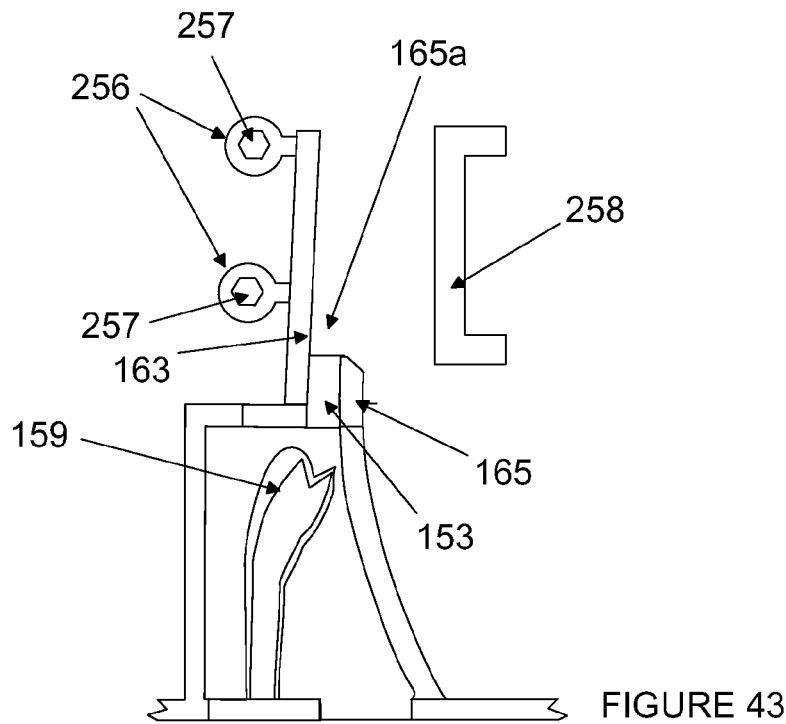
FIG. 43 is a top view of a scalpel blade remover having two insertion extensions for a transparent blade shield, said extensions extending up from a floor of a bottom half of a sharps box.

FIG. 43 is a top view of a scalpel blade remover as previously described with walls 163 and 165 and having a further protection wall 258 restricting location a recently disengaged scalpel blade falling or moved from disengaging zone 165*a* onto a floor section between walls 163 and 258. So restricting the location of the recently disengaged blade prevents it from falling atop or being mixed with other sharps being held in the bottom half of the sharps box. Two insertion extensions 256 comprise cylindrical upward extensions from a floor of a bottom half of a sharps box, each extension 256 defining a hexagonal bore 157 for receiving a hexagonal insert of a transparent cover to secure it into position relative to the blade remover. A separate part is formed apart from the bottom half of the sharps box so that the cover or blade shield may be formed of transparent polymer instead of the opaque polymer of the sharps box.

Figure 44:
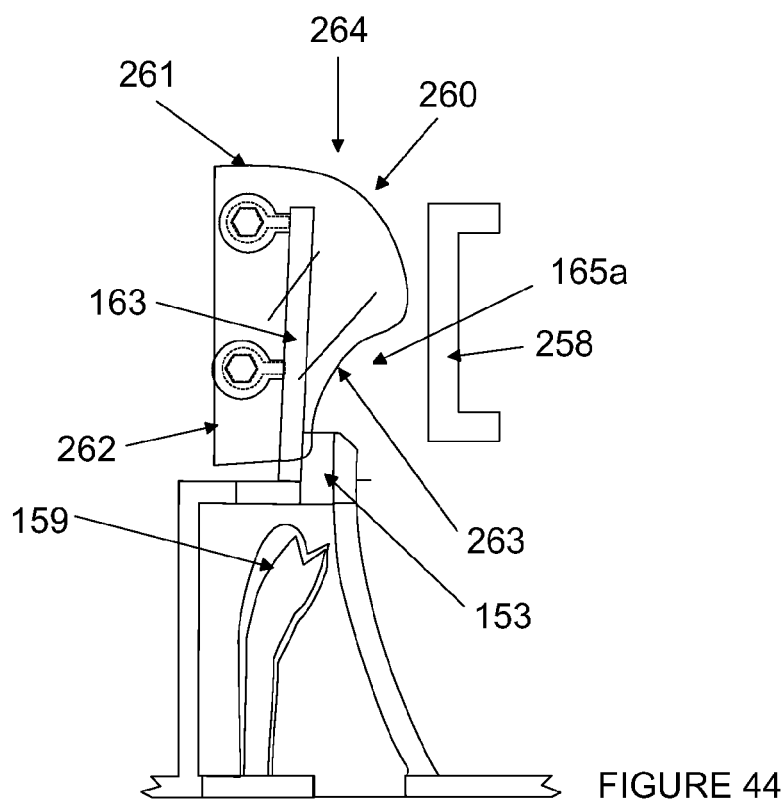
FIG. 44 is the scalpel blade remover of FIG. 43 with the transparent blade shield inserted in the insertion extensions, fixing the shield above a blade disengagement zone.
Figure 45:
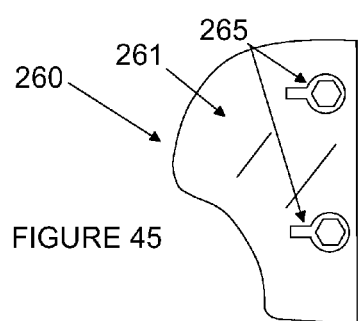
FIGS. 45 through 48 are respectively bottom, top, left and right views of the transparent blade shield of FIG. 44.
Figure 46:
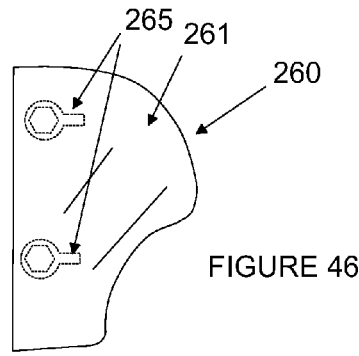
Figure 47:
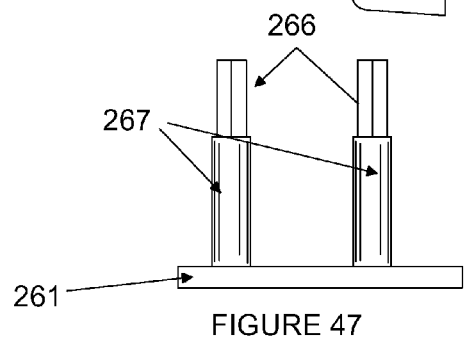
Figure 48:
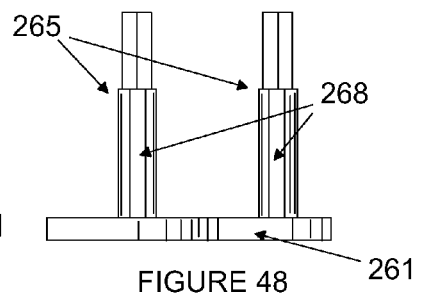

FIG. 44 is the scalpel blade remover of FIG. 43 with the transparent blade shield 260 inserted in the insertion extensions 256, fixing an arcuate transparent plate 261 above a blade disengagement zone 165*a*. A distal part of plate 261 is wider than a proximate part 262, with a convex curve 263 defined by a right side of plate 261 to accommodate up and down motion of a scalpel blade handle being engaged with the blade remover to remove a scalpel blade. An exposed part of wall 153, across which a scalpel blade and a front part of the scalpel handle will travel, is only partly covered by plate 261, whereafter plate 261 immediate extends to the right to protect a user from a springing disengaged blade or spatters of blood or other fluids which often are emitted when a scalpel blade is snapped free of its handle.

Figure 49:
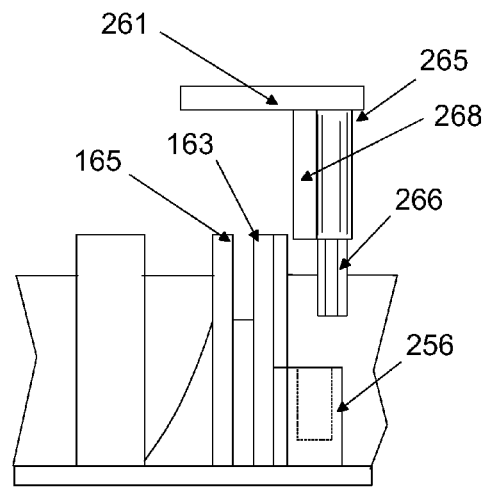
FIGS. 49 and 50 are each views in direction 264 of the blade remover of FIG. 44, respectively with the transparent blade shield about to be inserted in the two insertion extensions and with the transparent blade shield inserted in the two insertion extensions.
Figure 50:
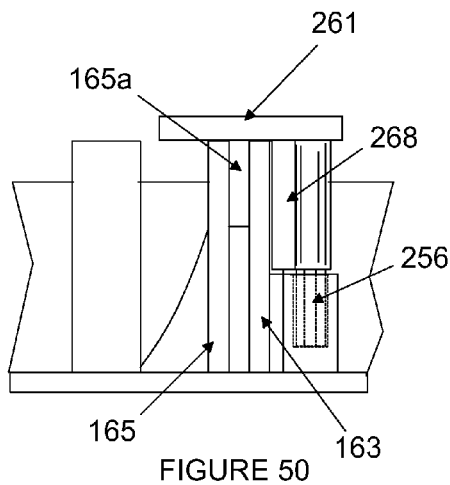

FIGS. 45 through 48 are respectively bottom, top, left and right views of the transparent blade shield 260 of FIG. 44, showing two post extensions 265 downward from plate 261, each comprising a cylindrical section 267 and a polygonal section 266. FIGS. 49 and 50 are each views in direction 264 of the blade remover of FIG. 44, respectively with the transparent blade shield 260 about to be inserted in the two insertion extensions 256 and with the transparent blade shield 260 inserted in the two insertion extensions 256, where an underside of plate 261 is impressed upon a top edge of wall 163. Shield 260 may either be removable from insertion extensions 256 or fixed by adhesives at manufacture. Removability provides the user with the option of retaining the shield 260 in place or using the scalpel blade remover without shield 260. There is a need for a scalpel blade remover having a transparent shield in line of sight between a disengaging scalpel blade and a user's face and eyes, as provided by the instant embodiment of FIGS. 43 through 50.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

I claim:

1. A sharps container box having a separately unitarily molded top half and bottom half incorporating into one of four sidewalls of the bottom half a scalpel blade remover adapted to remove a scalpel blade from a scalpel handle, each scalpel blade having a rear edge which abuts a rear surface of a neck of the scalpel handle in a locking relationship, the handle further having a blade locking portion provided at a front end thereof and grooves provided along the periphery of the blade locking portion, the scalpel blade also having a slot for receiving the grooves of the blade locking portion of the scalpel handle, the grooves being slidable in the slot and passing through a wider opening at a portion of the slot to permit the blade to be removed from the blade locking portion, the scalpel blade remover comprising:
   (a) a vertical rectangular opening defined in a sidewall and a bottom floor's edge of the bottom half, extending upward and inward from the bottom floor's edge a ramp at from 30 degrees to 60 degrees to an elevation from 0.25 to 1.5 inches from the bottom floor, the ramp being supported by a left wall, back wall, and right wall;
   (b) a notched extension extending rearward from near an inside surface of the sidewall to the left of the rectangular opening, the notched extension being curved at a distal end into a space inwardly normal to the rectangular opening, whereon said distal end is a defined notch inward directed, the notched extension having an elevation greater than the back wall by greater than 0.25 inches, and a cutout is defined in the ramp around the notched extension allowing deflection of said distal end to the left;
   (c) a left guide wall extending inward from the back wall, rising from the bottom floor to an elevation more than 0.25 inches above the top of the back wall, and having a right side aligned with a right edge of the rectangular opening;
   (d) a right guide wall extending inward from the back wall, rising from the bottom floor to an elevation more than 0.25 inches above the top of the back wall, and having a left side aligned spaced apart from the right side of the left guide wall by a thickness of the blade locking portion;
   (e) the right wall extending from a front edge of the right guide wall convexly along the ramp to a right edge of the rectangular opening; and
   (f) the blade remover is adapted so that:
   (i) a tip of a scalpel blade fixed to a scalpel handle may be moved past the rectangular opening to force a bottom edge of the blade to slide up the ramp and come to rest on a top edge of the back wall resulting in said distal end to be deflected substantially to the left; and
   (ii) the distal end of the notched extension is urged to the right to engage the rear edge of the scalpel blade, whereupon a user draws the scalpel handle outward from the sidewalls to disengage the scalpel blade from the scalpel handle.

2. The sharps container box of claim 1 wherein the right guide wall has an inward directed length of from one third to two thirds that of the left guide wall, each of the left and right guide walls having the same elevation.

3. The sharps container box of claim 1 wherein the elevation of the notched extension rises to 0.5 inches or more above the elevation of the back wall.

4. The sharps container box of claim 1 wherein a distance between said distal end and the back wall is 0.5 inches or greater.

5. The sharps container box of claim 1 wherein a distance between said distal end and the back wall is 0.25 inches or less.

6. The sharps container box of claim 5 wherein the left guide wall extends from a near edge and to the left along a top edge of the back wall, forming a rounded corner at the intersection of a back wall section and an inward directed section.

7. The sharps container box of claim 6 wherein left guide wall rounded corner is adapted to have a distance from said distal end sufficient to allow leftward deflection of the rear edge of the scalpel blade during disengagement from the scalpel handle.

8. The sharps container box of claim 6 wherein left guide wall rounded corner has a distance from said distal end of about 0.5 inches or greater.

* * * * *